US012245970B2

(12) United States Patent
Bruder et al.

(10) Patent No.: US 12,245,970 B2
(45) Date of Patent: *Mar. 11, 2025

(54) SELF-HEATING COMPRESS FOR MOIST HEAT DELIVERY

(71) Applicant: THE HILSINGER COMPANY PARENT, LLC, Mansfield, MA (US)

(72) Inventors: Mark H. Bruder, Alpharetta, GA (US); Rodney L. Dobson, Greer, SC (US)

(73) Assignee: THE HILSINGER COMPANY PARENT, LLC, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/648,907

(22) Filed: Apr. 29, 2024

(65) Prior Publication Data
US 2024/0268994 A1 Aug. 15, 2024

Related U.S. Application Data

(63) Continuation of application No. 17/222,488, filed on Apr. 5, 2021, now Pat. No. 11,998,480, which is a continuation-in-part of application No. 16/366,310, filed on Mar. 27, 2019, now Pat. No. 12,156,831, which is a continuation-in-part of application No. 16/202,879, filed on Nov. 28, 2018, said application
(Continued)

(51) Int. Cl.
*A61F 7/02* (2006.01)
*A61F 7/00* (2006.01)

(52) U.S. Cl.
CPC ........ *A61F 7/02* (2013.01); *A61F 2007/0004* (2013.01); *A61F 2007/023* (2013.01); *A61F 2007/0258* (2013.01); *A61F 2007/0266* (2013.01)

(58) Field of Classification Search
CPC ................ A61F 7/02; A61F 2007/0004; A61F 2007/023; A61F 2007/0258; A61F 2007/0266
See application file for complete search history.

(56) References Cited

U.S. PATENT DOCUMENTS

| | | | | |
|---|---|---|---|---|
| 4,252,119 | A | * | 2/1981 | Coates .................. A61F 15/001 604/306 |
| 4,372,318 | A | * | 2/1983 | Viesturs .................... A61F 7/02 607/109 |

(Continued)

OTHER PUBLICATIONS

EyeGiene Hot Eye Compress, Amazon.com, accessed Mar. 1, 2022, publication / on-sale date unknown.

*Primary Examiner* — Guy K Townsend
(74) *Attorney, Agent, or Firm* — Perilla Knox & Hildebrandt LLP

(57) ABSTRACT

A system for delivering thermal therapy to a treated body portion of a subject. The system preferably includes a therapy compress having at least one pocket or retainer, and at least one self-heating element configured for removable insertion within the at least one pocket of the therapy compress. In some example embodiments the therapy compress is in the form of an eye mask having first and second eye-covering lobes, each eye-covering lobe having a pocket for receiving a self-heating element. In some example embodiments the at least one self-heating element is air or oxygen activated, for example including a zinc-based self-heating material.

25 Claims, 24 Drawing Sheets

Related U.S. Application Data

No. 17/222,488 is a continuation-in-part of application No. 16/107,200, filed on Aug. 21, 2018, which is a continuation-in-part of application No. 15/443,199, filed on Feb. 27, 2017, now abandoned.

(60) Provisional application No. 63/005,752, filed on Apr. 6, 2020, provisional application No. 62/591,929, filed on Nov. 29, 2017, provisional application No. 62/548,774, filed on Aug. 22, 2017, provisional application No. 62/430,430, filed on Dec. 6, 2016, provisional application No. 62/301,999, filed on Mar. 1, 2016.

(56) References Cited

U.S. PATENT DOCUMENTS

| | | | | |
|---|---|---|---|---|
| 4,516,564 | A * | 5/1985 | Koiso | A61F 7/034 607/114 |
| 4,525,410 | A * | 6/1985 | Hagiwara | A01N 59/16 424/641 |
| 5,948,010 | A * | 9/1999 | Adamec | A61F 7/02 607/108 |
| 6,409,746 | B1 * | 6/2002 | Igaki | A61F 7/03 607/114 |
| 6,537,308 | B2 * | 3/2003 | Burkhart | A61F 7/02 604/303 |
| 6,823,860 | B2 * | 11/2004 | Igaki | A61F 7/03 126/263.05 |
| 7,722,782 | B2 | 5/2010 | Coffey et al. | |
| 8,535,363 | B1 * | 9/2013 | Lewis | A61F 7/007 219/528 |
| 8,636,786 | B2 * | 1/2014 | Biser | A61F 7/02 607/107 |
| 8,784,391 | B1 * | 7/2014 | Biser | A61F 7/02 604/294 |
| 9,004,059 | B2 | 4/2015 | Sesock et al. | |
| 9,024,360 | B1 | 5/2015 | Huffer et al. | |
| 9,278,796 | B2 | 3/2016 | Huffer et al. | |
| 9,592,149 | B2 * | 3/2017 | Hidaka | A61F 7/034 |
| 9,642,736 | B2 | 5/2017 | Laubach et al. | |
| 9,642,740 | B2 * | 5/2017 | Bruder | A61L 15/44 |
| 9,872,795 | B2 | 1/2018 | Laubach et al. | |
| 9,925,087 | B2 * | 3/2018 | Bruder | A61F 13/01021 |
| 10,046,325 | B2 | 8/2018 | Beckerdite et al. | |
| 10,105,259 | B2 * | 10/2018 | Bruder | A61F 13/00 |
| D844,795 | S * | 4/2019 | Bruder | A61F 13/00 D24/206 |
| D870,906 | S * | 12/2019 | Bruder | A61F 13/00 D24/206 |
| D871,598 | S * | 12/2019 | Bruder | A61F 13/00 D24/206 |
| 10,973,674 | B2 | 4/2021 | Laubach et al. | |
| 11,998,480 | B2 * | 6/2024 | Bruder | A61F 7/02 |
| 2002/0032153 | A1 * | 3/2002 | Whitehouse | A61K 38/1825 514/8.1 |
| 2004/0035410 | A1 * | 2/2004 | Igaki | A61F 9/04 126/263.05 |
| 2005/0118383 | A1 * | 6/2005 | Cargill | A61F 7/02 428/36.1 |
| 2005/0278008 | A1 * | 12/2005 | Ladmer | A61F 7/02 607/114 |
| 2008/0141437 | A1 * | 6/2008 | Braunecker | A61F 7/03 2/206 |
| 2009/0104243 | A1 * | 4/2009 | Utkhede | A61F 9/0017 424/423 |
| 2009/0149925 | A1 * | 6/2009 | MacDonald | A61F 7/034 436/7 |
| 2009/0287282 | A1 * | 11/2009 | Biser | A61F 7/02 607/109 |
| 2009/0287283 | A1 * | 11/2009 | Biser | A61F 7/02 607/109 |
| 2010/0146849 | A1 | 6/2010 | Coffey et al. | |
| 2010/0163011 | A1 | 7/2010 | Tinker et al. | |
| 2010/0312317 | A1 * | 12/2010 | Baltazar | A61F 7/02 607/108 |
| 2011/0178585 | A1 * | 7/2011 | Biser | A61F 7/02 607/109 |
| 2011/0208279 | A1 * | 8/2011 | Sanker | A61F 7/02 607/109 |
| 2011/0307041 | A1 * | 12/2011 | Floyd | A61F 7/10 523/105 |
| 2013/0131613 | A1 * | 5/2013 | Elkins | A61F 9/04 604/303 |
| 2013/0174835 | A1 | 7/2013 | Tinker et al. | |
| 2013/0317459 | A1 * | 11/2013 | Bruder | A61F 13/00063 604/290 |
| 2014/0186420 | A1 * | 7/2014 | Utkhede | A61P 27/02 514/530 |
| 2014/0277303 | A1 * | 9/2014 | Biser | A61F 7/02 607/104 |
| 2014/0288624 | A1 * | 9/2014 | Wasko | A61F 7/02 607/109 |
| 2014/0330222 | A1 * | 11/2014 | Bruder | A61F 13/124 604/290 |
| 2014/0345543 | A1 * | 11/2014 | Saita | A61F 7/034 122/21 |
| 2015/0057701 | A1 * | 2/2015 | Kelleher | A61H 23/0245 606/204.15 |
| 2015/0088236 | A1 * | 3/2015 | Bruder | A61F 13/01021 607/108 |
| 2016/0120692 | A1 * | 5/2016 | Chen | A61F 7/03 607/109 |
| 2016/0206476 | A1 * | 7/2016 | Robertson | A61F 9/045 |
| 2017/0049614 | A1 * | 2/2017 | Paulson | A61F 9/04 |
| 2017/0216088 | A1 * | 8/2017 | Johnson | A61F 7/02 |
| 2017/0252210 | A1 * | 9/2017 | Bruder | A61F 9/045 |
| 2017/0266035 | A1 * | 9/2017 | Kuo | G08C 17/02 |
| 2017/0266053 | A1 * | 9/2017 | Rodriguez | A61F 13/124 |
| 2018/0289531 | A1 * | 10/2018 | Thomas | A61F 7/007 |
| 2018/0338864 | A1 * | 11/2018 | Paulson | A61F 7/007 |
| 2019/0000666 | A1 * | 1/2019 | Bruder | A61F 13/00063 |
| 2019/0053940 | A1 * | 2/2019 | Biser | A61F 7/0241 |
| 2019/0083299 | A1 * | 3/2019 | Rozanski | A61F 7/02 |
| 2019/0125579 | A1 * | 5/2019 | Habib | A61F 9/04 |
| 2019/0159929 | A1 * | 5/2019 | Bruder | A61F 9/04 |
| 2019/0183671 | A1 * | 6/2019 | Baltazar | C09K 5/10 |
| 2021/0267793 | A1 * | 9/2021 | Bruder | A61F 7/02 |
| 2024/0268994 | A1 * | 8/2024 | Bruder | A61F 7/03 |

\* cited by examiner

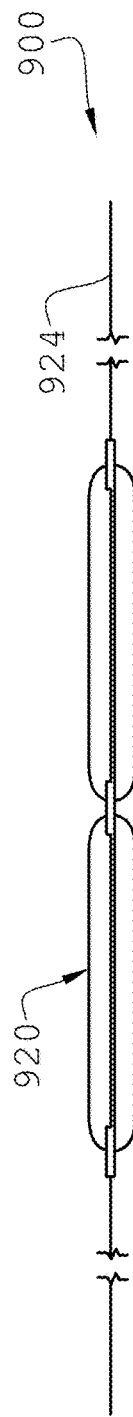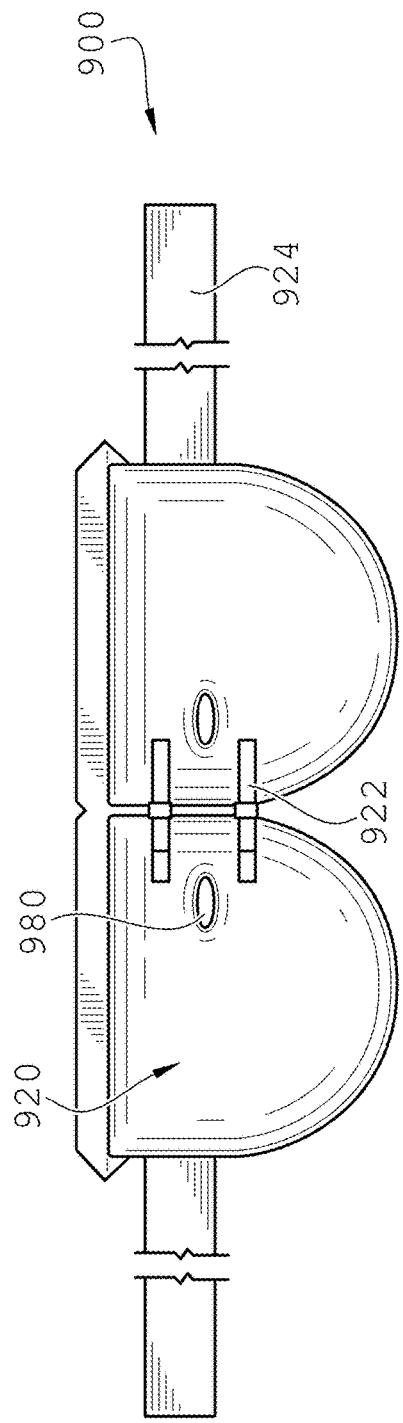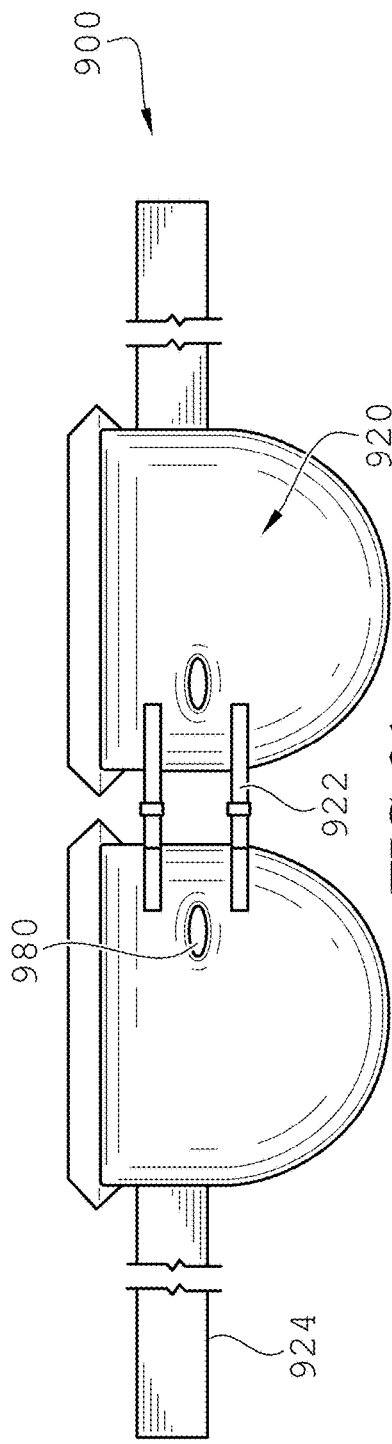

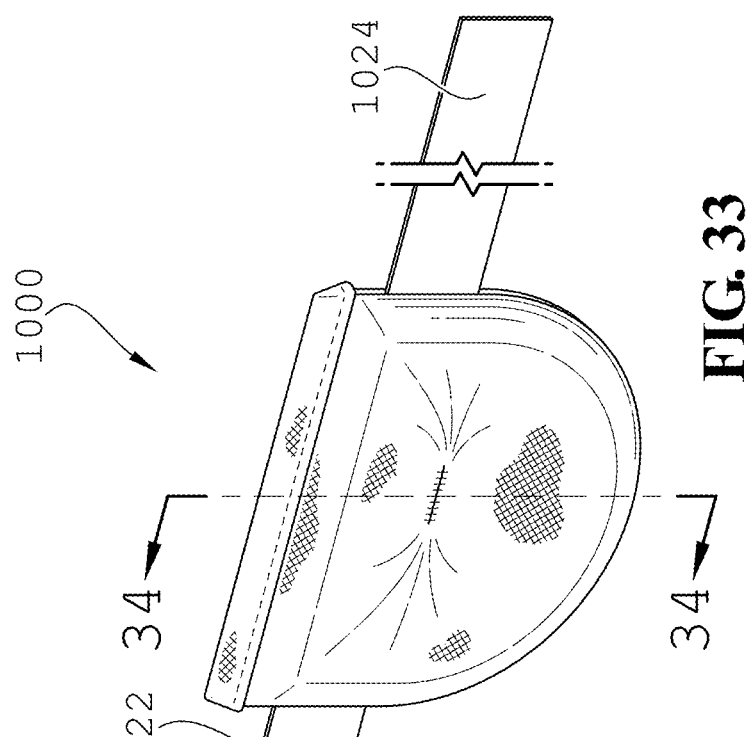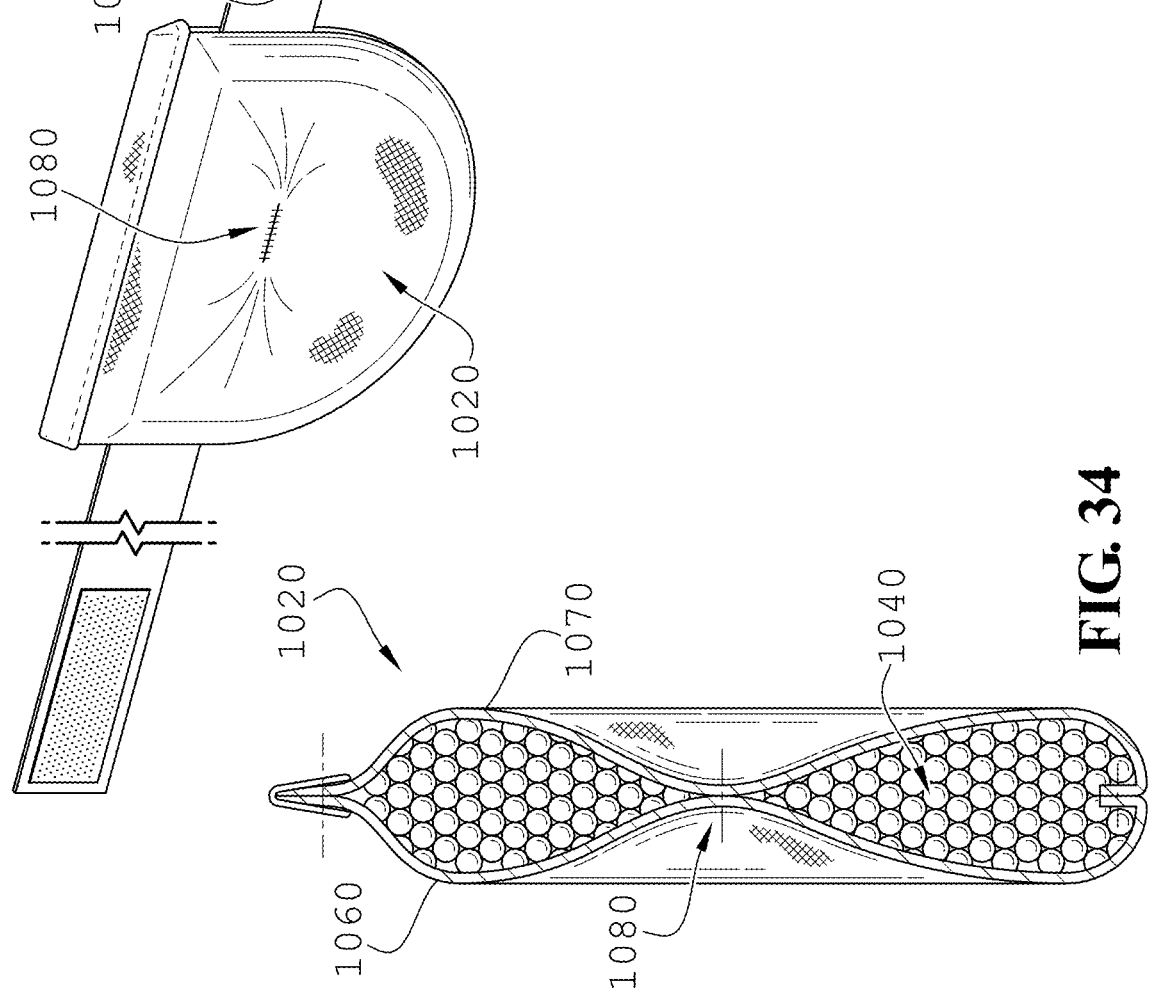

SELF-HEATING COMPRESS FOR MOIST HEAT DELIVERY

CROSS-REFERENCE TO RELATED APPLICATIONS

This application is a continuation of U.S. Non-Provisional patent application Ser. No. 17/222,488 filed Apr. 5, 2021, which claims priority to U.S. Provisional Patent Application Ser. No. 63/005,752 filed Apr. 6, 2020; this application is also a continuation-in-part of U.S. Non-Provisional patent application Ser. No. 16/366,310 filed Mar. 27, 2019, which is a continuation-in-part of U.S. Non-Provisional patent application Ser. No. 16/202,879 filed Nov. 28, 2018, which claims priority to U.S. Provisional Patent Application Ser. No. 62/591,929 filed Nov. 29, 2017; Application Ser. No. 17/222,488 is also a continuation-in-part of U.S. Non-Provisional patent application Ser. No. 16/107,200 filed Aug. 21, 2018, which is a continuation-in-part of U.S. Non-Provisional patent application Ser. No. 15/443,199 filed Feb. 27, 2017, which claims priority to U.S. Provisional Patent Application Ser. No. 62/301,999 filed Mar. 1, 2016, and to U.S. Provisional Patent Application Ser. No. 62/430,430 filed Dec. 6, 2016; and U.S. Non-Provisional patent application Ser. No. 16/107,200 also claims priority to U.S. Provisional Patent Application Ser. No. 62/548,774 filed Aug. 22, 2017; all of which are hereby incorporated herein by reference.

TECHNICAL FIELD

The present invention relates generally to the field of hot or cold thermal therapy, such as for example ophthalmic medical therapy or palliative care of the eye or other body part of a human or animal subject by application of thermal therapy with a therapeutic thermal compress.

BACKGROUND

Various conditions of the eye may require medical or palliative care. For example, blepharitis is a common and ongoing condition where the eyelids become inflamed (swollen), with oily particles and bacteria coating the eyelid margin near the base of the eyelashes. This condition causes irritation, itchiness, redness, dry eye and stinging or burning of the eyes. While the underlying causes of blepharitis are not completely understood, it can be associated with a bacterial eye infection, symptoms of dry eyes or certain types of skin conditions such as acne rosacea. Anterior blepharitis affects the outside of the eyelid where the eyelashes are attached. This can be caused by bacterial (or sometimes viral) infection. If left untreated, anterior blepharitis can lead to thickened and inward-turned or outward-turned eyelids and even vision problems from in-turned eyelashes damaging the cornea. Posterior blepharitis is a condition that results from a dysfunction of the eye's tiny oil glands (meibomian glands) in the eyelids at the base of the eyelashes. When meibomian glands become clogged from posterior blepharitis, it can cause a stye or chalazion to form. Posterior blepharitis can also lead to thickened eyelid margins and crusty eyelids.

An estimated 40.9 million people in the United States aged 18 or older wear contact lenses. The International Workshop on Contact Lens Discomfort, published in 2013, put forth dryness of the eyes as a primary reason for contact lens intolerance. When a contact lens is placed on the eye, the tear film structure becomes altered resulting in a pre-lens thinned lipid layer and a post-lens thinned aqueous layer. As a result of this disruption from the contact lens, the tear film tends to have an increased rate of evaporation leading to poor wetting on the surface of the contact lens and inadequate lubrication on the surface of the eye. This is further exacerbated if the patient has an already unstable lipid layer due to the presence of meibomian gland dysfunction (MGD). MGD is considered by many to be the leading cause of dry eye disease throughout the world and is a chronic and progressive condition that can contribute to a poor quality lipid layer and lead to contact lens discomfort. Contact lens wearers often report dry eye symptoms and show signs of MGD including gland atrophy, thinned lipid layer, and increased tear film instability. It has been shown that in many patients with intolerance to contact lenses, MGD has been observed. Therefore, treatment of MGD may support the functioning of the meibomian glands and lead to improvement in patient contact lens comfort.

Hygienic home treatment of such ocular disorders can be a two-step process. First, the patient softens the debris and scurf that accumulates around the eye. The debris can be softened by applying a warm compress, diluted baby shampoo, or a specialized liquid solution to the eyelid margin. This first step is intended to prepare the debris for removal while preventing further irritation to the eye. Second, the patient can attempt to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris and scurf free from the base of the eyelashes and unclogging the pores of the meibomian glands, the patient may improve the overall health of the eyelid margin; thereby reducing irritation, burning, and other symptoms related to the disorder.

Thermal therapy can also be used for medical or palliative care of a human or animal subject or patient, for example by delivering moist heat or cold to the eye region. In example applications, thermal therapy can be used to unblock glands in the eye to help treat dry eye. Moist heat may also be used to help reduce elevated intraocular pressure to either treat or help prevent open-angle glaucoma. Delivery of medications to the eyes, such as for treatment of blepharitis may be enhanced by application of thermal therapy in combination with the medication. Applying heat to the inner eyelid may also help safely remove gland obstructions and stagnant gland content. Moist heat thermal therapy of the eyes may also be beneficial to extend comfortable wearing time of contact lenses.

Many currently known eye treatment masks are not designed to securely fit the eye, causing issues in some forms of therapeutic treatment. For example, when a patient uses a continuous positive airway pressure (CPAP) machine for treatment of sleep apnea, air can sometimes blowback from the mask of the CPAP machine into the user's eyes, causing dryness of the eyes. Known eye masks and eye compresses may not fit securely to the eye and have not been found entirely successful in protecting the eyes from this blow-back dryness.

In other instances, it is desirable to maintain a relatively steady temperature (i.e., within a specified temperature range) for an extended period of time during thermal (hot or cold) therapy by application of a thermal therapeutic compress to a body part (back, neck, eye, head, arm, leg, torso, foot, ankle, knee, hip, shoulder, elbow, wrist, hand, or other body part). Many known therapeutic compresses are not capable of sustaining a therapy temperature for sustained periods desired for such treatment. In other instances, external heat sources such as a microwave oven may not be available or convenient for heating a therapeutic compress, or a longer duration application of heat therapy than provided by the initial heating of a compress with an external heat source may be desirable.

Needs exist for improvements to ophthalmic medical therapy or palliative care of the eye. Further needs exist for improvements to thermal therapeutic compresses to allow longer-term sustained thermal treatment within a specified temperature range. It is to the provision improved therapeutic eye mask system and treatment methods meeting these and other needs that the present invention is primarily directed.

SUMMARY

In example embodiments, the present invention provides a therapeutic mask or compress system for treatment of the eyes, generally including at least one, and in particular embodiments two separate eye coverage portions, wherein each of the eye coverage portions is configured to deliver moist heat therapy to the eye area of a human or animal patient. The mask is configured to be worn on the head of the patient with one of the eye coverage portions positioned over at least one eye, and in particular embodiments with eye coverage portions positioned over both eyes of the patient.

In one aspect, example embodiments of the invention relate to a self-heating eye mask for delivering thermal therapy to an eye region of a human subject. The eye mask preferably includes a therapy compress comprising at least one eye-covering portion configured for application to the eye region of the human subject. The eye mask preferably also includes at least one self-heating element contained within the at least one eye-covering portion of the therapy compress, comprising at least one reactant material reactive with air to generate an exothermic reaction and release heat for delivery to the eye region of the human subject.

In another aspect, example embodiments of the invention relate to a self-heating eye mask for delivering thermal therapy to a human subject. The eye mask preferably includes a therapy compress comprising first and second eye-covering portions each configured for application to a respective eye region of the human subject. The eye mask preferably also includes first and second self-heating elements, the first self-heating element contained within the first eye-covering portion of the therapy compress and the second self-heating element contained within the second eye-covering portion of the therapy compress, the first and second self-heating elements each comprising at least one reactant material reactive with air to generate an exothermic reaction and release heat for delivery to the eye region of the human subject.

In another aspect, example embodiments of the invention relate to a self-heating eye mask for delivering thermal therapy to an eye region of a human subject. The eye mask preferably includes a therapy compress having at least one eye-covering portion configured for application to the eye region of the human subject. The eye mask preferably also includes at least one self-heating element contained within the at least one eye-covering portion of the therapy compress, comprising at least one reactant material reactive with air to generate an exothermic reaction and release heat, and further comprising a hydrophilic material, whereby heat released from the reactant material effects release of moisture from the hydrophilic material to deliver moist heat therapy to the eye region of the human subject.

In still another aspect, example embodiments of the invention relate to a self-heating therapy system for delivering thermal therapy to a treated body portion of a subject. The system preferably includes a therapy compress configured for attachment to a treated body part, the compress comprising an outer shell containing a hydrophilic fill material, and at least one self-heating element configured for engagement with the therapy compress to deliver heat to release moisture from the hydrophilic fill material and effect delivery of moist heat therapy to the treated body part.

In another aspect, example embodiments of the invention relate to a self-heating therapy system for delivering thermal therapy to a treated body portion of a subject. The system preferably includes a therapy compress configured for attachment to a treated body part and having an outer shell containing a hydrophilic fill material, and at least one self-heating element configured for engagement with the therapy compress to deliver heat to release moisture from the hydrophilic zeolite particulate fill material and effect delivery of moist heat therapy to the treated body part.

In another aspect. example embodiments of the invention relate to a self-heating therapy system for delivering thermal therapy to a treated body portion of a subject. The system preferably includes at least one self-heating element having at least one reactant material reactive with air to generate an exothermic reaction and release heat, and a therapy compress configured for attachment to a treated body part, the compress comprising an outer shell containing a hydrophilic fill material, and retention means for retaining the at least one self-heating element.

In further embodiments of the invention, the eye mask or compress comprises at least one eye coverage portion, at least one securing strap attached to the eye coverage portion(s) for securing the eye coverage portion(s) over the eye of the patient, and a fill material enclosed within each eye coverage portion. The eye coverage portions are formed from a moisture-permeable material comprising antimicrobial properties wherein the fill material is configured to absorb and release moisture through the moisture-permeable material. Each eye coverage portion has a front side, configured to rest against the face of the patient in contact with the area around one or both of the user's eyes, and a back side opposite the front side directed away from the user. In example embodiments, each eye coverage portion also includes a generally centrally located dimple or recess on the front side or both sides, forming a retracted non-contact area configured allow space between the compress and the eye area of the subject, to prevent the application of excessive heat on and around the cornea, preventing conditions such as corneal warping, while allowing moist heat therapy to reach the eyelid and surrounding eye area.

In another aspect, the invention relates to an eye compress for delivery of moist heat to a patient. In example forms, the eye compress includes at least one enclosure containing a fill material capable of absorbing and releasing moist heat for therapeutic delivery to the patient, the enclosure having a first side and an opposite second side, with the fill material disposed between the first and second sides, and wherein the first side is configured for application to an eye or other body portion of the patient. In example embodiments, the eye compress also includes a stitched or sutured segment joining the first side and the second side, wherein the stitched segment is configured to be positioned over a cornea of the eye of the patient, to prevent application of excess heat transmission from the fill material to the cornea of the patient or user.

In still another aspect, the invention relates to a method of providing moist heat therapy to an eye area of a human or animal subject. In example forms, the method includes providing a therapeutic device comprising at least one eye cover enclosure with a first side and a second side, a seam or stitched segment joining together the first and second sides to form a recessed non-contact area, and a hydrophilic fill material contained within the first and second sides of the eye cover enclosure. The first side of the eye cover enclosure at least partially comprises a moisture-transmissive material allowing passage of moisture therethrough for absorption into and release from the fill material. The stitched segment is configured to be positioned over the cornea of the eye of the human or animal subject to prevent excessive heat exposure to the cornea. Additionally, in example embodiments the eye cover enclosure at least partially comprises antimicrobial material.

In still another aspect, the invention relates to thermal therapeutic systems, apparatus, devices and methods for maintaining a relatively steady temperature (i.e., within a specified temperature range) for an extended period of time during thermal (hot or cold) therapy by application of a thermal therapeutic compress to a body part (back, neck, eye, head, arm, leg, torso, foot, ankle, knee, hip, shoulder, elbow, wrist, hand, or other body part). In example embodiments, a therapeutic compress capable of sustaining a therapy temperature for sustained periods is provided. In particular embodiments, a thermal therapy compress incorporating one or more phase-change materials is provided.

In another aspect, the invention relates to a system for delivering thermal therapy to a treated body portion of a subject. The system preferably includes a therapy compress having at least one pocket, and at least one self-heating element configured for removable insertion within the at least one pocket of the therapy compress.

In further example embodiments, the present invention relates to a mask or compress for thermal treatment and/or delivery of medication to the eyes, and surrounding sinus and facial areas of a subject or patient.

In further example embodiments, a thermal therapeutic compress may be configured and provided for application to the neck, back, or other body part.

In particular applications, embodiments of the invention further relate to a moist heat delivery device with heat-loss preventive structures, thermal protective measures, and/or antimicrobial properties.

In further example embodiments, a phase-change material is incorporated into a thermal therapy compress for sustained thermal therapy within a desired temperature range for an extended period of time.

In further example embodiments, a therapeutic eye mask or thermal compress system incorporates an oxygen- or otherwise-activated self-heating element for delivery of heat, and for example moist heat, to a treated body part of a human or animal subject. The self-heating element may be integral with the compress or may be removable and replaceable. The self-heating element may be the sole source of heating the compress or may supplement or sustain the heating applied by another external heating source such as a microwave oven.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of preferred embodiments of the invention, and are not restrictive of the invention, as claimed.

BRIEF DESCRIPTION OF THE DRAWINGS

FIG. 29 is a side view of the therapeutic eye mask system of FIG. 28.

FIG. 30 shows a front view of the therapeutic eye mask system of FIG. 28.

FIG. 31 shows an alternative configuration of the therapeutic eye mask system of FIG. 30.

FIG. 33 is a perspective view of the therapeutic eye mask system of FIG. 32.

FIG. 34 is a cross-sectional view of the therapeutic eye mask system of FIG. 33 at section line 34-34.

DETAILED DESCRIPTION OF EXAMPLE EMBODIMENTS

Figure 1:
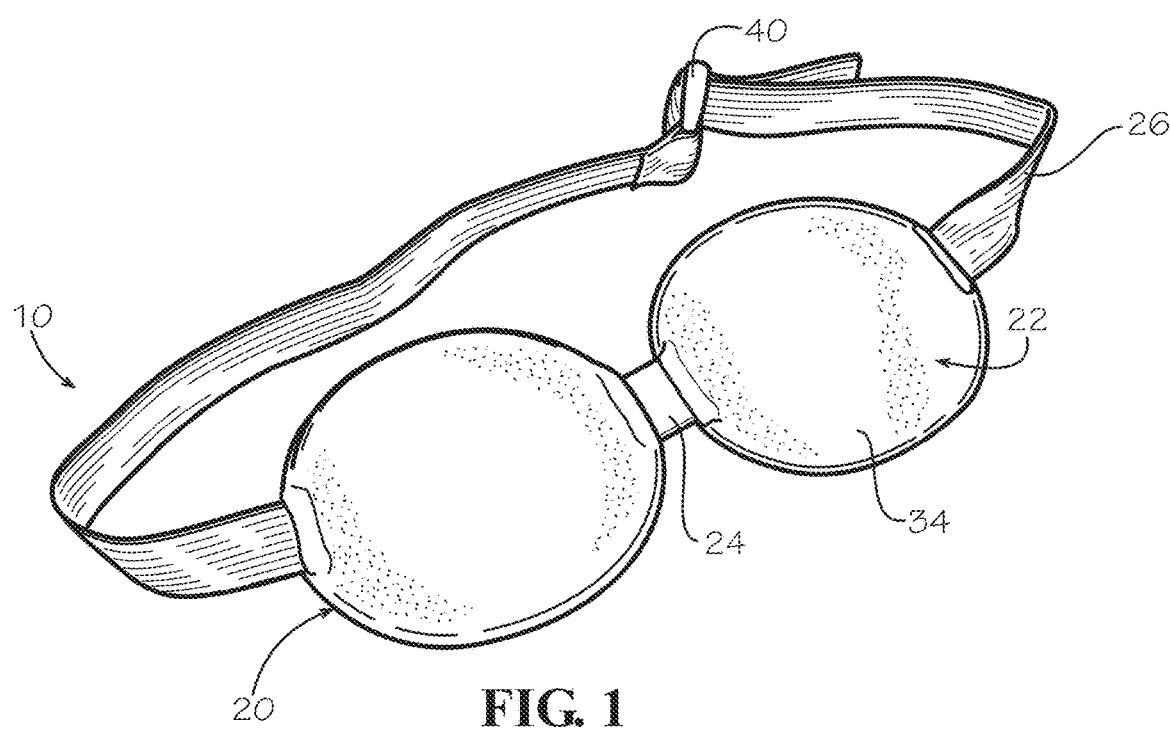
FIG. 1 is a perspective view of a therapeutic eye mask system according to an example embodiment of the invention.
Figure 2:
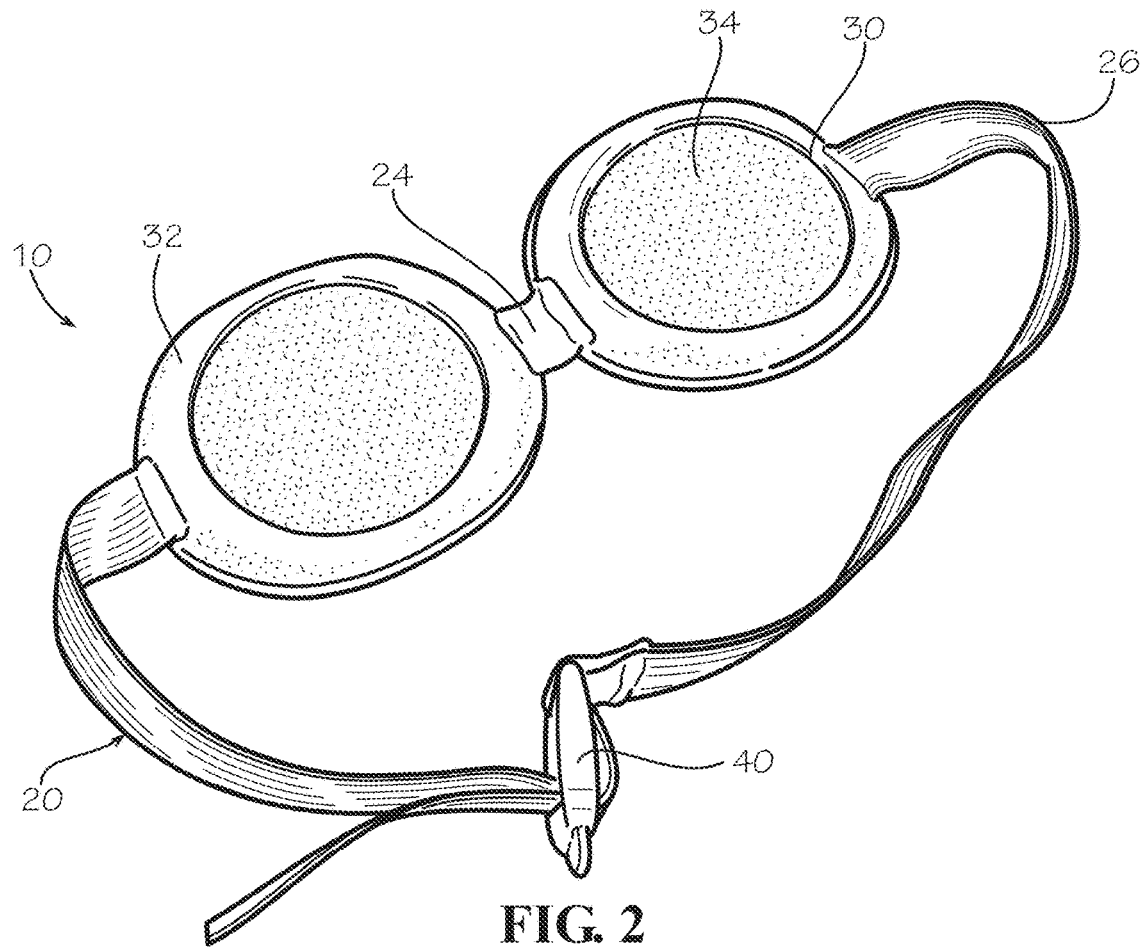
FIG. 2 shows a back view of the therapeutic eye mask system depicted in FIG. 1.
Figure 3:
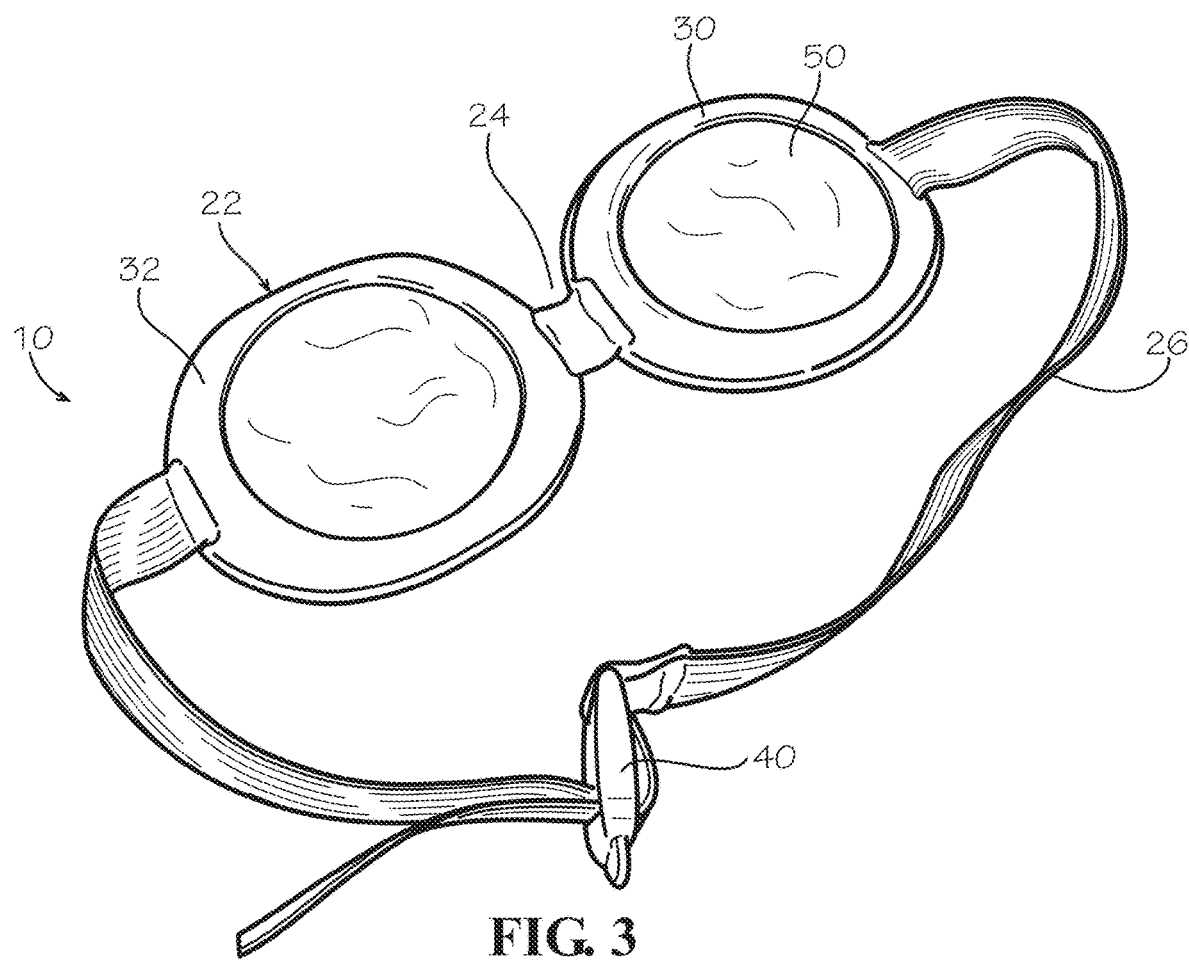
FIG. 3 shows the therapeutic eye mask system depicted in FIG. 2 including detachable pods.
Figure 4A:
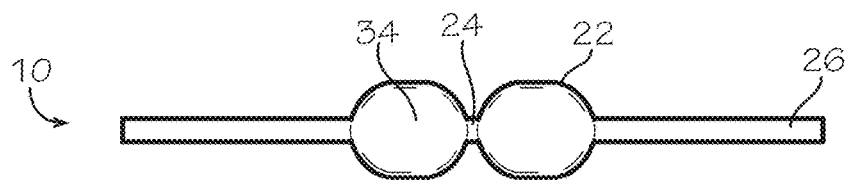
FIGS. 4A-C show a front, back and side view of the therapeutic eye mask system of FIG. 1.
Figure 4B:
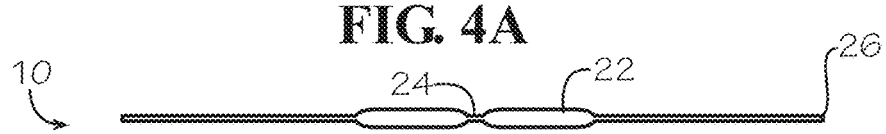
Figure 4C:
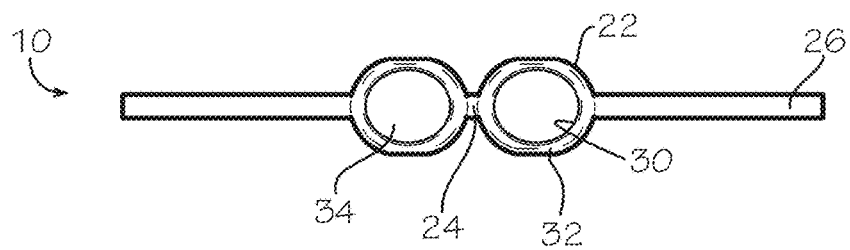
Figure 5:
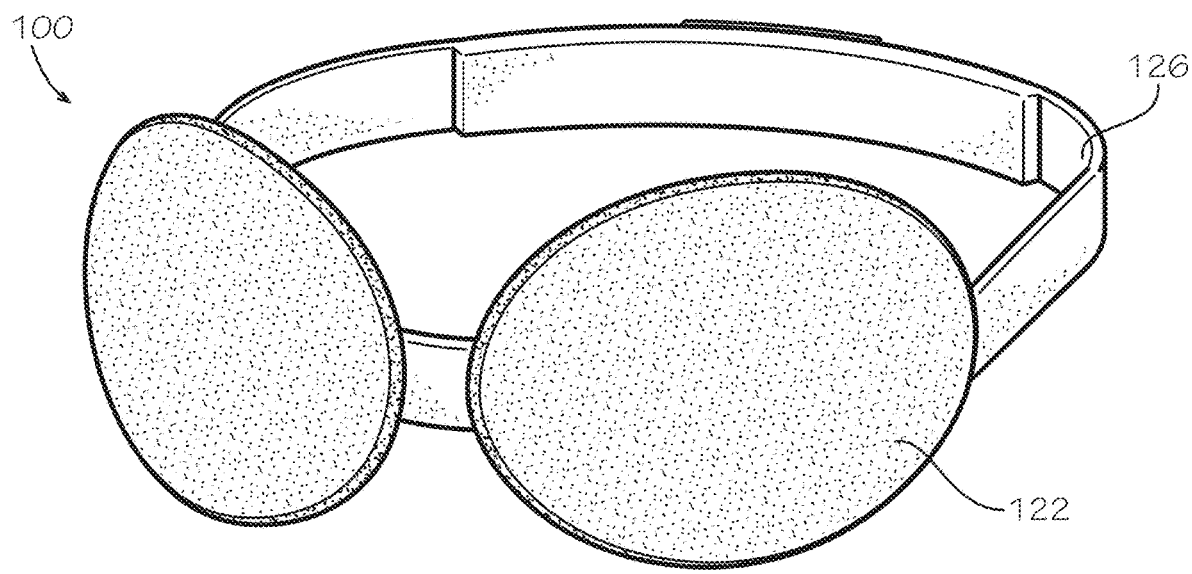
FIG. 5 is a perspective view of a therapeutic eye mask system according to another example embodiment of the invention.
Figure 6:
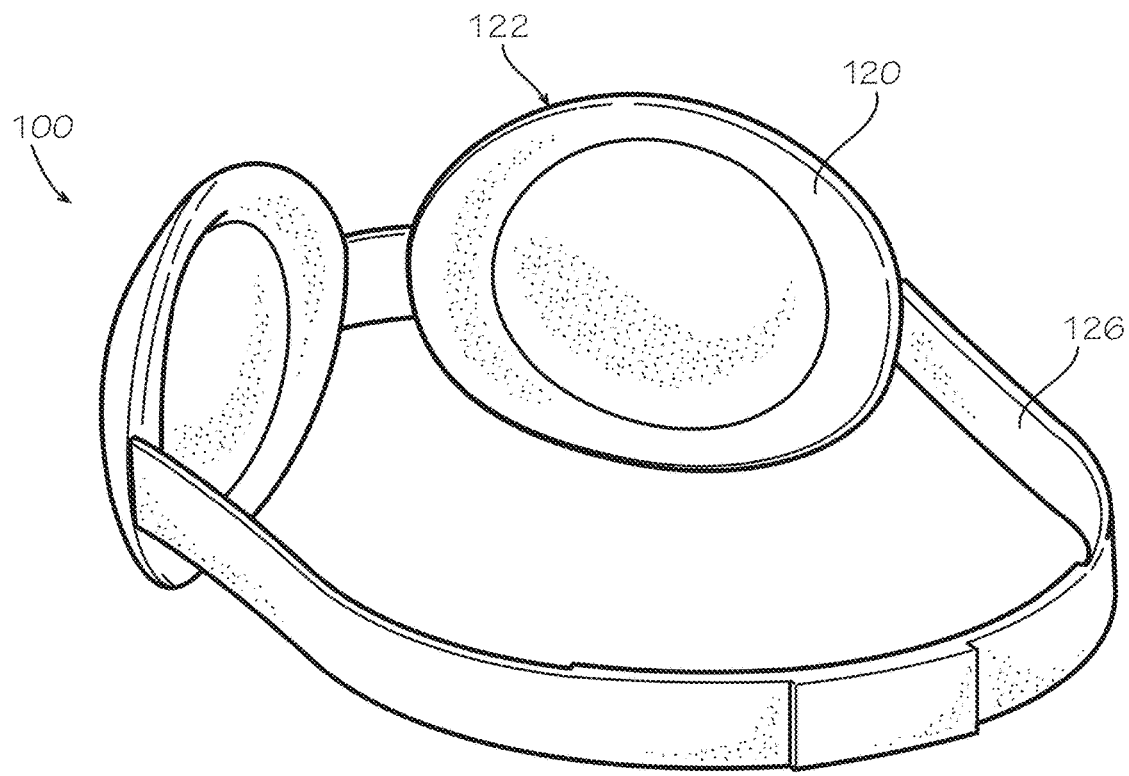
FIG. 6 shows a back view of the therapeutic eye mask system of FIG. 5.
Figure 7A:
FIGS. 7A-C show a front, back and side view of an eye mask portion for use in a therapeutic eye mask system according to another example embodiment of the invention.
Figure 7B:
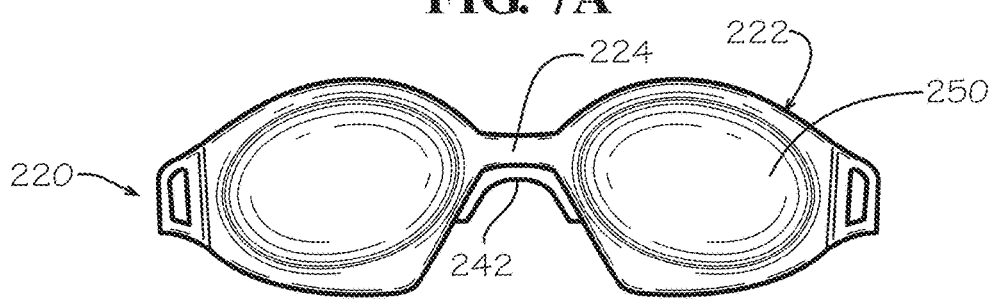
Figure 7C:
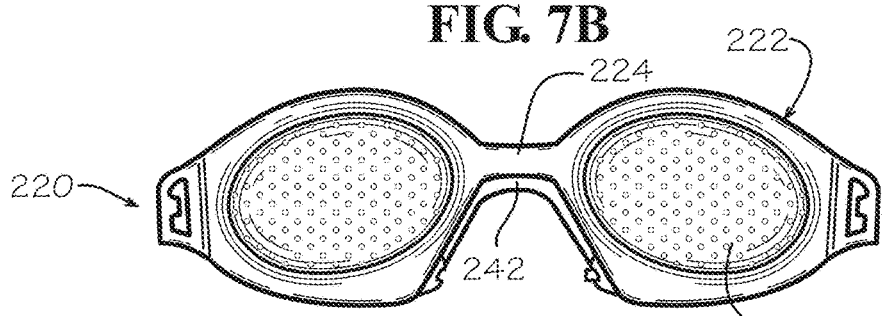
Figure 8A:
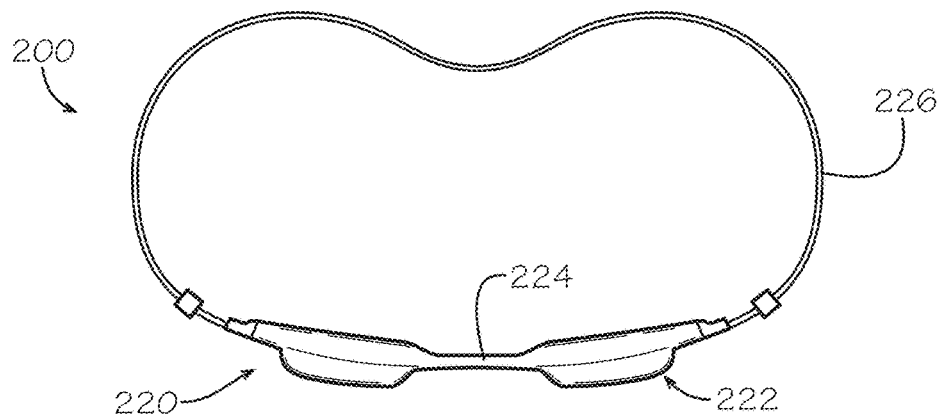
FIGS. 8A-C show a front, top and side views of a therapeutic eye mask system with the eye mask portion of FIGS. 7A-C.
Figure 8B:
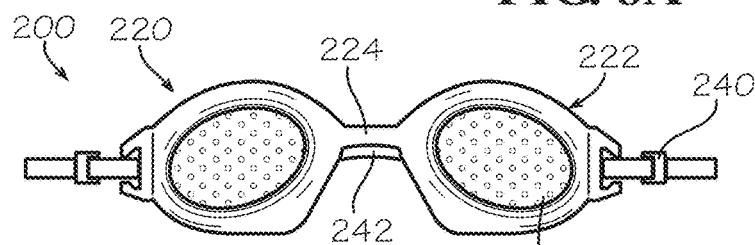
Figure 8C:
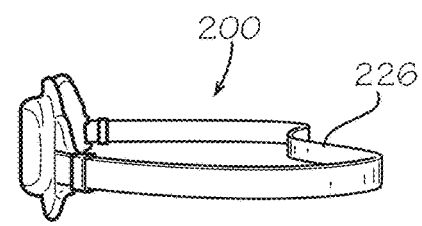

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-20 show a therapeutic eye mask system according to example embodiments of the present invention. The therapeutic eye mask system 10, shown in FIGS. 1-4, generally includes an eye mask 20 and at least one detachable therapy pod 50. The eye mask 20 can include two separate eye coverage portions 22 connected by a nose bridge 24 and a securing strap 26. The mask 20 is configured to be worn on the head of a human patient with one of the eye coverage portions 22 positioned over each eye of the patient. In example embodiments, the securing strap 26 is positioned around the user's head to hold the eye coverage portions 20 against the eyes of the user.

In example embodiments, the mask 20 can have a monolithic uniform construction or may be separate pieces fastened together, for example by stitching, adhesive, fasteners or other attachment means. In example embodiments, the mask 20 is constructed of a lightweight and durable material. The mask 20 can be made of a soft and flexible material, for example, foam or polyester. It can be constructed of perforated thermoformed foam to improve breathability. The mask 20 can be constructed from laminated foam or soft-flexible, open-cell foam with polyester fabric. In particular examples, the mask 20 is constructed from a 2 lb./ft$^3$, ⅜" thick polyether polyurethane foam, flame laminated to matte black polyester fiber interlock fabric on both sides. Alternatively, the mask 20 is constructed from polyester, rayon, spandex, silk or other natural and/or synthetic fabrics or materials. The mask material can optionally be selected to have insulative or heat-transmissive properties to affect the temperature transferred from the mask to the patient's eyes, ensuring safety. The material may optionally be washable for reuse, or alternatively can be a single-use disposable product. In example embodiments, the mask 20 may be constructed of a material containing nanobeads comprising an antimicrobial metal.

The mask 20 depicted in FIGS. 1-4 includes two eye coverage portions 22. The eye coverage portions 22 are designed to be independent structures such that each can independently conform to the respective eye region of the patient. The eye coverage portions 22 can each include a receiver 30 for holding a detachable therapeutic pod 50. The receivers 30 are configured to hold the pods 50 in position over the patient's eyes when the mask 20 is worn. In example embodiments, the receivers 30 are permanently-formed indents or pockets in the eye coverage portion 22. For example, the indents or pockets can be positioned on the side of the mask that directly faces the eyes of the patient when worn. In use, two removable pods 50 are received in the mask 20, one within each of the receivers 30. Each eye coverage portion 22 can optionally include an eye cushion 32 and an eye cover 34. The eye cushion 32 is configured to surround the receiver 30 and provide padding on a portion of the mask 20 that abuts the users face when worn. The eye cover 34 is configured to cover the outside of the eye coverage portion 22. In alternative embodiments, the mask 20 does not include an eye cover 34 and the eye coverage portion 22 is formed from a circular frame that is open when a detachable pod 50 is not in the receiver 30. The eye coverage portions 22 can be a substantially round shape as depicted in FIGS. 1-4 or can be an oval, elliptical, polygonal, angled or another non-round shape.

The eye coverage portions 22 can be connected by a nose bridge 24 and a securing strap 26. The nose bridge 24 can be formed from a flexible and/or elastic material that allows the nose bridge to fit the face shape of a variety of users. In alternate embodiments, the nose bridge 24 is adjustable. In the depicted embodiments, the securing strap 26 is formed from a strap extending between the eye coverage portions 22. The securing strap 26 can include an adjustment mechanism 40 that allows the user to adjust the length of the strap. In alternate embodiments of the eye mask 100, depicted in FIGS. 5 and 6, the securing strap 126 is formed from two straps, each coupled at a first end to an eye coverage portion 122. The second end of each securing strap 126 is configured to be removably coupled to the other securing strap. The attachment mechanism can include snaps, ties, hook-and-loop fasteners or other releasable attachment mechanisms. The nose bridge 24 and securing strap 26 are configured so that the eye mask 20 can be one size to fit all or most users. Alternatively, the eye mask 10 can be produced in different sizes. The securing strap can also include a comfort wrap (not pictured). In alternate embodiments, the mask 20 can include dual supports to fit over the ears in place of the securing strap 26.

In other embodiments, the mask portion 220 of the therapeutic eye mask system 200 is shaped similar to swimming goggles. The eye coverage portions 222 have a teardrop shape with the top and bottom having a curved shape and the side adjacent the nose bridge being straight so as to follow the angle of the nose. The detachable pods 250 have a generally oval shape and are angled relative to the nose bridge 224. The nose bridge 224 can include a padded portion 242 to provide comfort when worn. The eye covers 234 can be perforated for breathability. The securing strap 226 of the depicted embodiment includes two adjustment mechanisms 240, one adjacent to each of the eye coverage portions 222.

Figure 9:
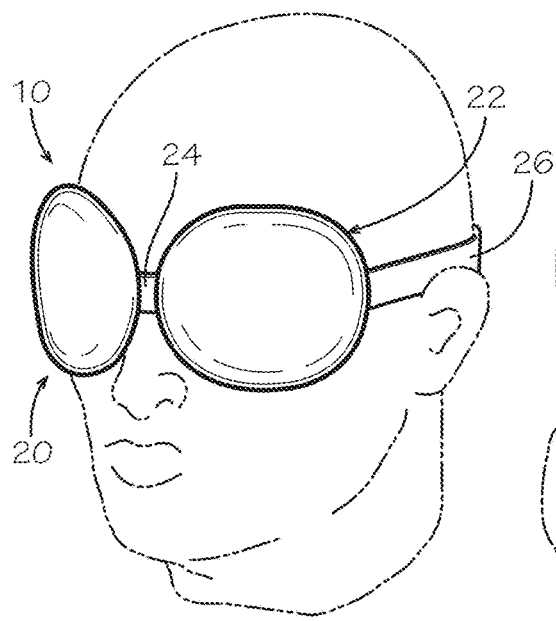
FIG. 9 shows the therapeutic eye mask of FIG. 1 worn by a human patient.
Figure 10:
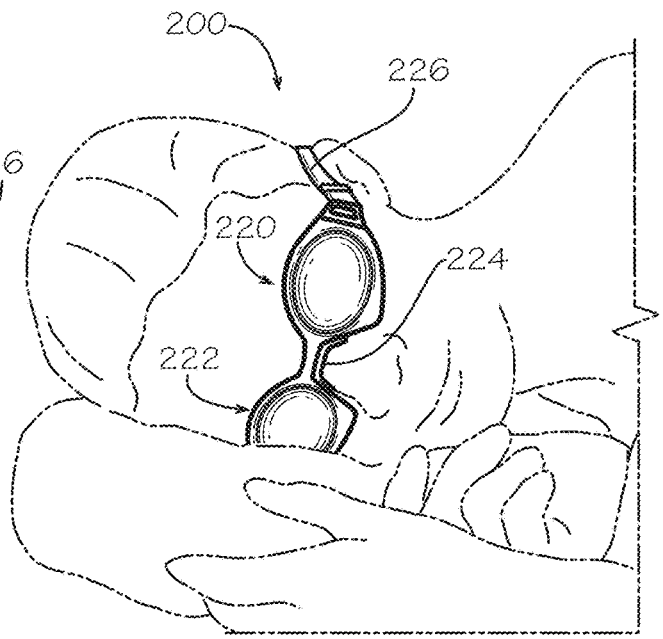
FIG. 10 shows the therapeutic eye mask of FIGS. 8A-C worn by a human patient.
Figure 11A:
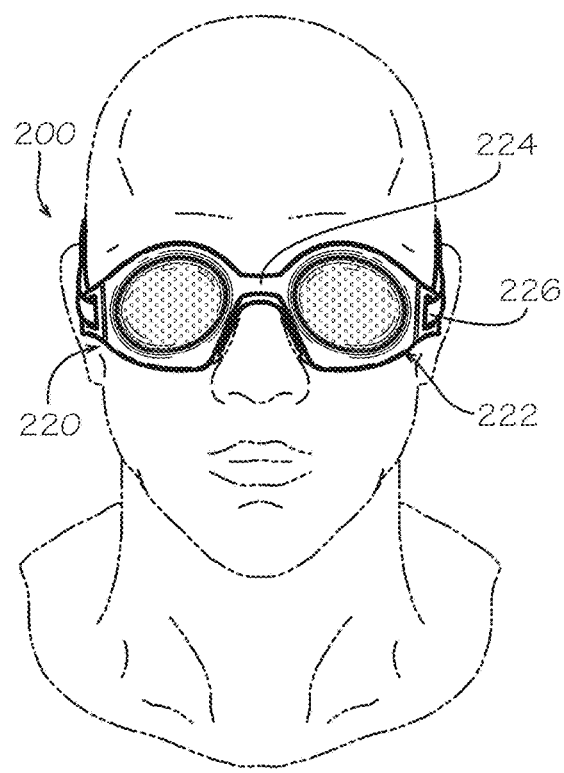
FIGS. 11A-B show the therapeutic eye mask of FIGS. 8A-C worn by a human patient.
Figure 11B:
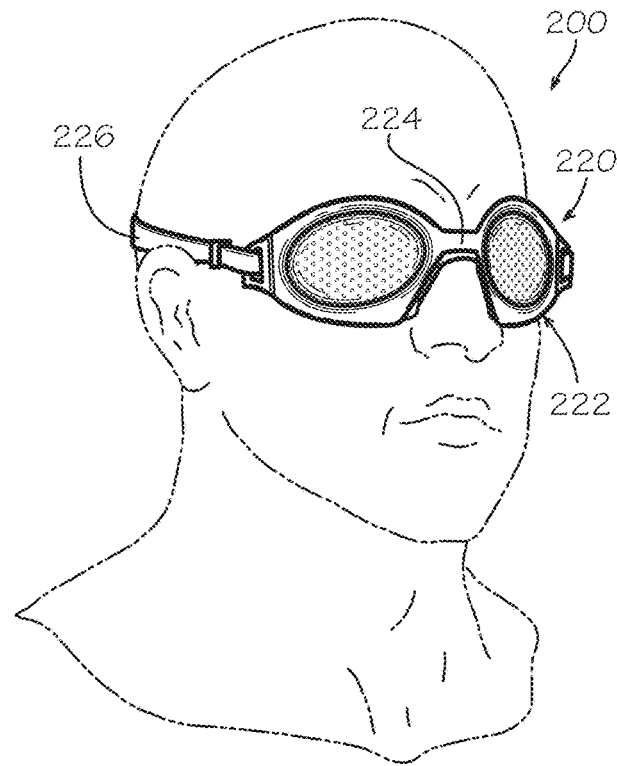

The mask 20, 220 portion of the therapeutic eye mask system 10, 200 is designed to fit securely to the patient's eye region with an eye coverage portion 22, 222 over each eye, the nose bridge 24, 224 positioned across the patient's nose and the securing strap 26, 226 extending around the back of the patient's head, as shown in FIGS. 9-11. The eye mask 20, 220 is designed such that it can be safe and comfortable to wear while sleeping, as shown in FIG. 10. The secure fit can also prevent air from being blown into the eye while the mask is being worn, for example when worn in combination with a CPAP machine. In example embodiments, the dual eye coverage portion design allows full conformance within the eye socket. The design also optionally allows heat and moist therapy to reach the sinuses to help relieve sinus pressure.

As discussed above, the eye coverage portions 22 of the mask 20 each include receivers configured to releasably secure a therapy pod 50. In example embodiments, the pods 50 have a soft outer shell construction that is able to contain a fill material capable of delivering therapy treatment, for example, moist heat and cold treatments. The outer shell of the pods 50 can be formed of fabric, non-wovens or other natural or synthetic materials, and is preferably thermally and moisture transmissive, to allow heat and/or moisture to pass through the shell to and from the fill material. Example fill materials include hydrophilic zeolite granules or particles, and optionally silver or other antimicrobial treatments, and/or other materials. The fill material can be loosely contained and held within the pod 50 such that each pod will conform to the eye area of the patient when worn. Alternatively, a liquid or gel fill material can be used. The pods 50 can be designed for single use or can be washable and re-usable.

In example embodiments, the fill material contained within the pods comprises a synthetic porous crystalline granular aluminosilicate zeolite, for example, a hydrophilic natural or synthetic zeolite, also referred to as a molecular sieve material, or other substances with similar properties. The fill material may further comprise other inert additives and physical matrices without affecting the antimicrobial and hydrous efficacies of the fill. The hydrophilic zeolite granules or beads are configured to repeatedly absorb and release moisture without substantially changing shape or form. Optionally, the pods comprise a granular fill material such as activated alumina, silica gel, bentonite or hydrophilic zeolite or molecular sieve material. In alternate embodiments, the pods comprise capsules or packets of non-granular material (e.g., gel, liquid), powder, or other materials. The pods or granules contained in the pods optionally also contain a metallic or other antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof deposited therein. For example, silver or another metal loading of the fill may be attained by the process of ion-exchange. In this process, a solution containing atomic silver or a composition of silver bathes or is passed through a bed of the fill granules. An ion-exchange column method may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules as known in the art may be applied to produce retention of the silver or other metals in the fill material of the pods. For example, the final content by weight of an atomic silver or silver composition, or other metals or antimicrobial agents, may be as high as twenty percent of the final loaded fill granules. In example embodiments, the loaded fill granules produced by ion-exchange will exhibit high retention of the silver or other metals even under subsequent exposure to fluids and microwave irradiation. The fill granules may comprise a blend of both metals loaded and unloaded (i.e., not containing metal) zeolite or other substance(s) retaining silver or other metals. The presence of the atomic silver or other metals preferably will not interfere with the useful properties of the fill granules such as the moisture desorption and adsorption properties which may be desirable in the use of the eye mask or compress system. The inherent hydrophilic nature of example forms of zeolite fill materials provides that substantial water content is available therein by absorption from the atmosphere. The water so absorbed may be sufficient for moist heat delivery applications, or may be supplemented by manually added water, for providing a microwave responsive water content of the eye mask or compress system. The compositions of silver or other metals used may include but are not limited to, metal compounds, and metal salts such as silver chloride and silver nitrate.

The presence of the silver or other metals within the fill granules optionally contained in the pods of the invention provides anti-microbial properties to the therapeutic eye mask system. The ion-exchange loaded fill granules will preferably retain the silver or other metals despite microwave heating as may be required in the use of the eye mask or compress system. Further, the retention of the silver or other metals within the fill granules provides assured antimicrobial performance in a reusable and potentially washable, if so desired, moist heat therapy compress. In other embodiments, the silver or other metals are incorporated into the cover material of the pods, the eye coverage portions, and/or other portions of the eye mask system, in addition to or instead of the fill granules. Alternatively, one or more non-metal antimicrobial materials and/or medications may optionally be incorporated into the fill material, the pods, the eye coverage portions, and/or other portions of the eye mask system.

Figure 12:
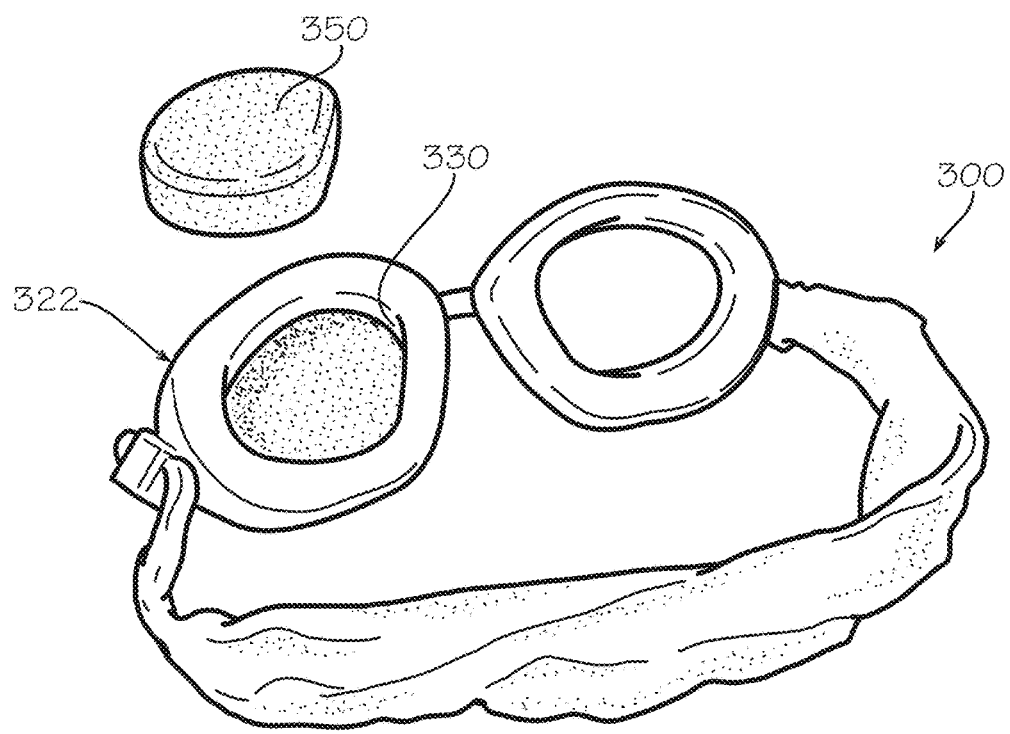
FIG. 12 shows a therapeutic eye mask system according to another example embodiment of the invention.
Figure 14:
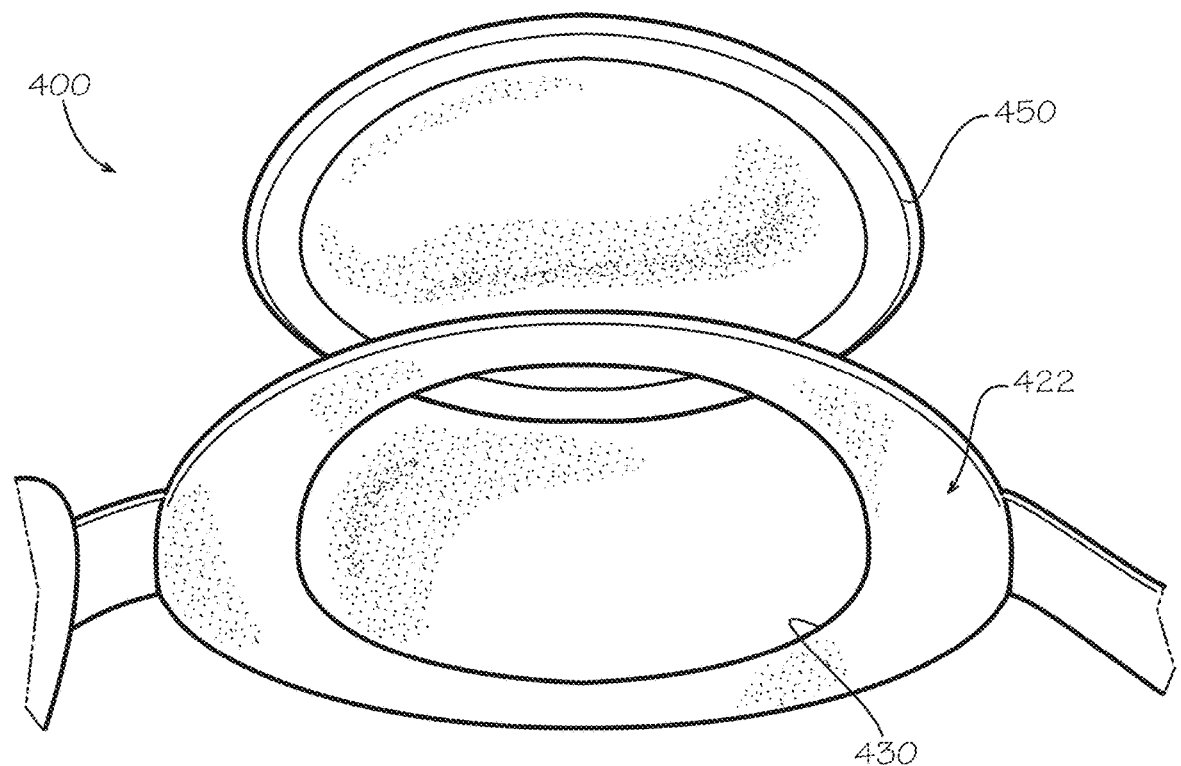
FIG. 14 shows a detailed exploded view of the therapeutic eye mask system of FIG. 13.
Figure 15:
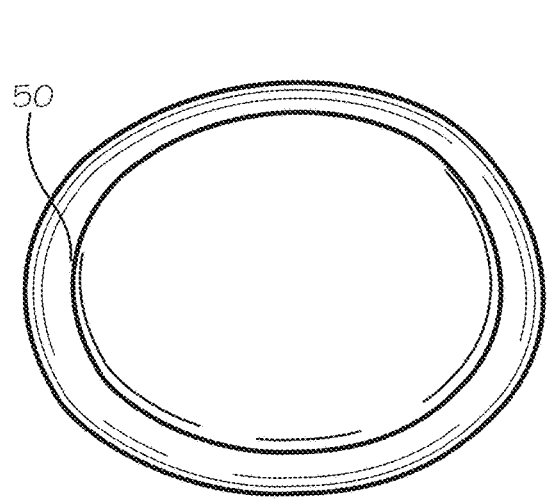
FIG. 15 shows a detachable pod for use in a therapeutic eye mask according to an example embodiment of the invention.
Figure 16:
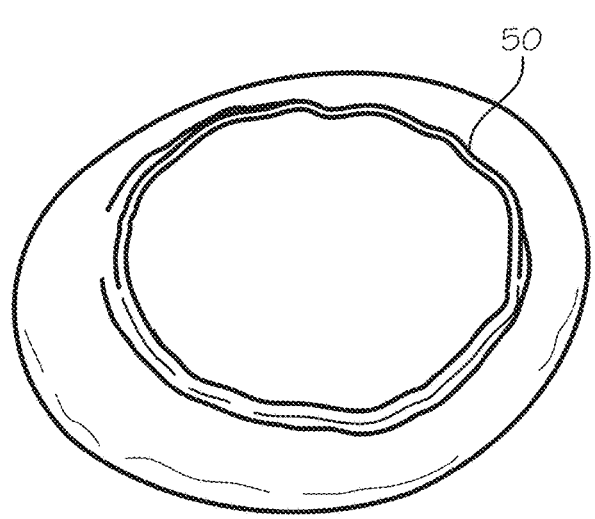
FIG. 16 shows a detachable pod according to another example embodiment of the present invention.
Figure 17:
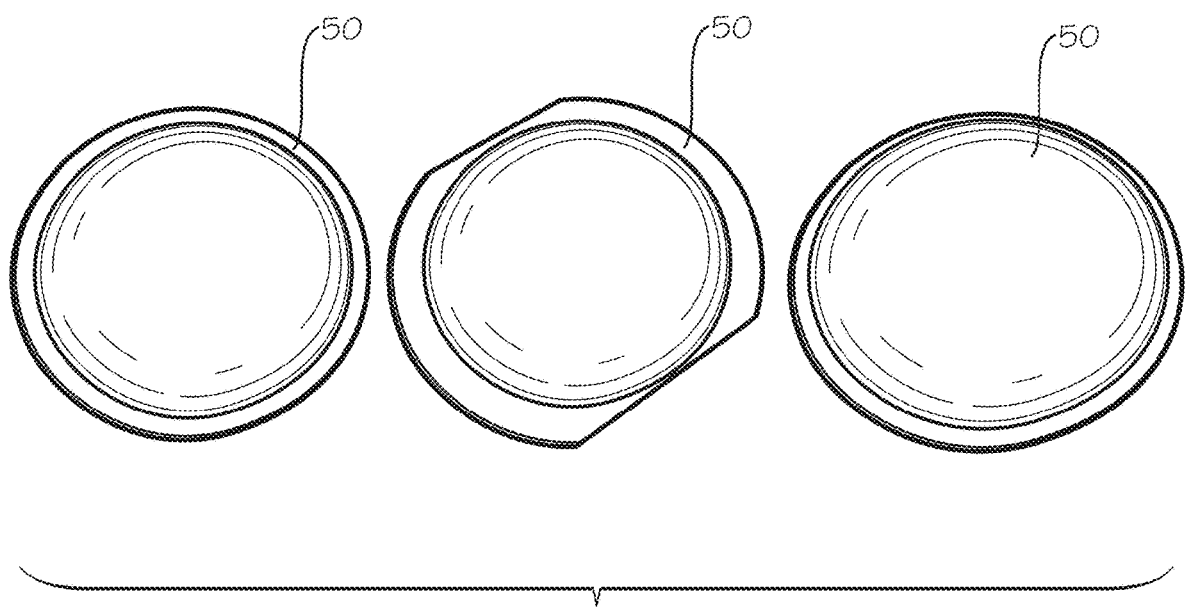
FIG. 17 shows detachable pods of varying shapes according to further example embodiments of the invention.
Figure 18:
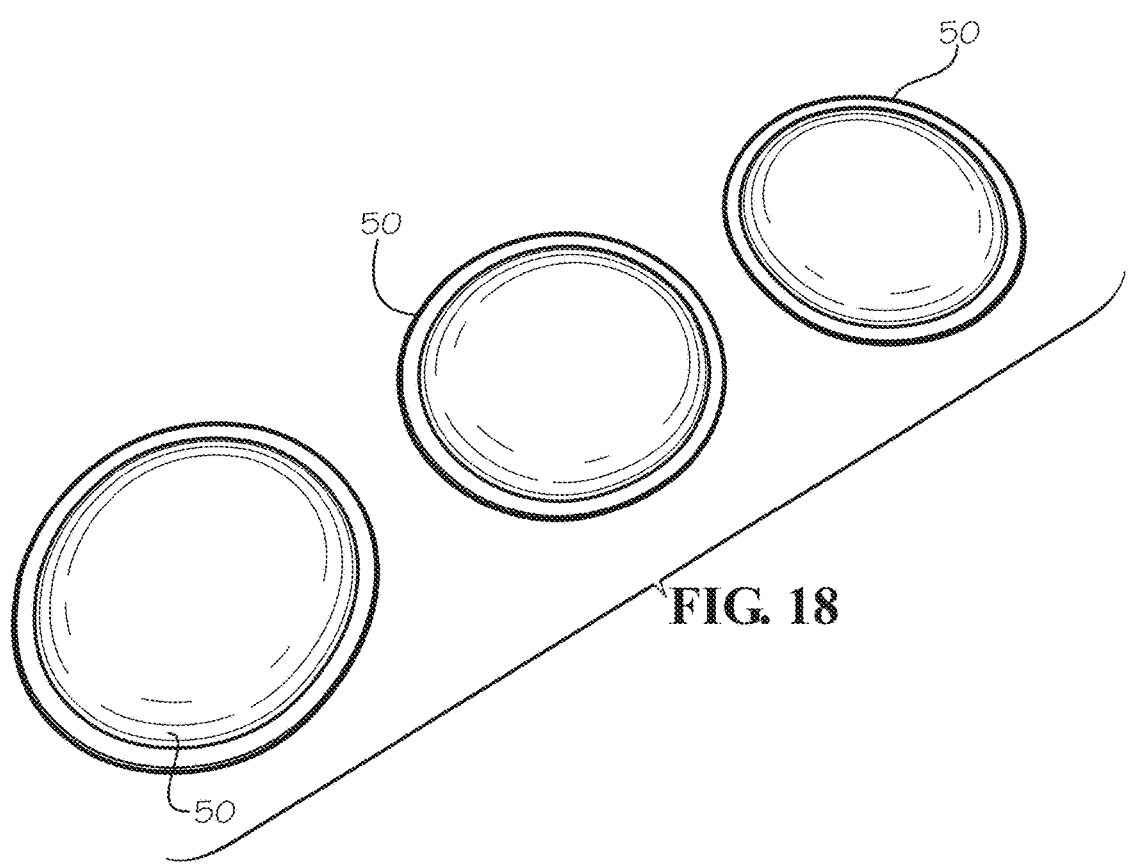
FIG. 18 shows detachable pods of varying sizes according to example embodiments of the invention.

In example embodiments of the therapeutic eye mask system 300, the pods 350 are push-fitted into the receivers 330 in each eye coverage portion 322, as shown in FIG. 12. The pods 350 can be detachably secured within the receivers 330 through the use of an attachment mechanism, for example, a hook-and-loop fastener material secured to both the pods and the receivers, by friction fit, or otherwise. Alternatively, the pods 350 are secured with a positive lock, clip, or a rigid snap. In other embodiments of the therapeutic eye mask system 400, the pods 450 can be slid into the receivers 430 through an opening in the top of the eye coverage portion 422, as shown in FIG. 14. The pods 50 may be round so that they are self-orienting when attached or inserted into the mask, or can be oval, elliptical, polygonal, angled or another non-round shape, as shown in FIG. 17. The pods can be provided in one or more different colors, for example, color coded based on their function. For example, a pod for moist heat treatment may be red and a pod for cool treatment may be blue. The pods 50 can also be provided in different sizes, as shown in FIG. 18. In example embodiments, the material and configuration of the mask form a seal against the wearer's face surrounding the eye area to prevent external airflow from drying the wearer's eyes or drying the pods or medication components positioned within the mask during use.

In use, the entire mask with the pods attached can be heated or cooled prior to use to provide therapy. The mask can be placed in the microwave to be heated or in the freezer to be cooled. Alternatively, the pods alone can be heated or cooled detached from the mask, then placed in the mask when they reach the desired temperature for treatment.

Additionally, various medicaments can be applied and used with respect to the pods. For example, one or more ophthalmic medications can be infused or injected into the formulation in the pods. Examples of medicants or therapeutic materials capable of delivery using the therapeutic device according to example forms of the invention include a jojoba formulation for treatment of the symptoms of dry eye, steroids such as clobetasol propionate, betamethasone dipropionate, amcinonide or loteprednol etabonate for treatments of diseases of the eyelid, such as chatazion, blepharitis or meibomian gland dysfunction. Medicants may also comprise a dietary or nutritional supplement composition comprising an effective amount of omega-3 fatty acids for treatment of dry eye or meibomianitis. Medicants may also comprise tetracycline, corticosteroids, androgens or androgen analogues. The medicant can also comprise a topical treatment to elevate the side effects of chemotherapy, including eyelash loss.

Figure 13:
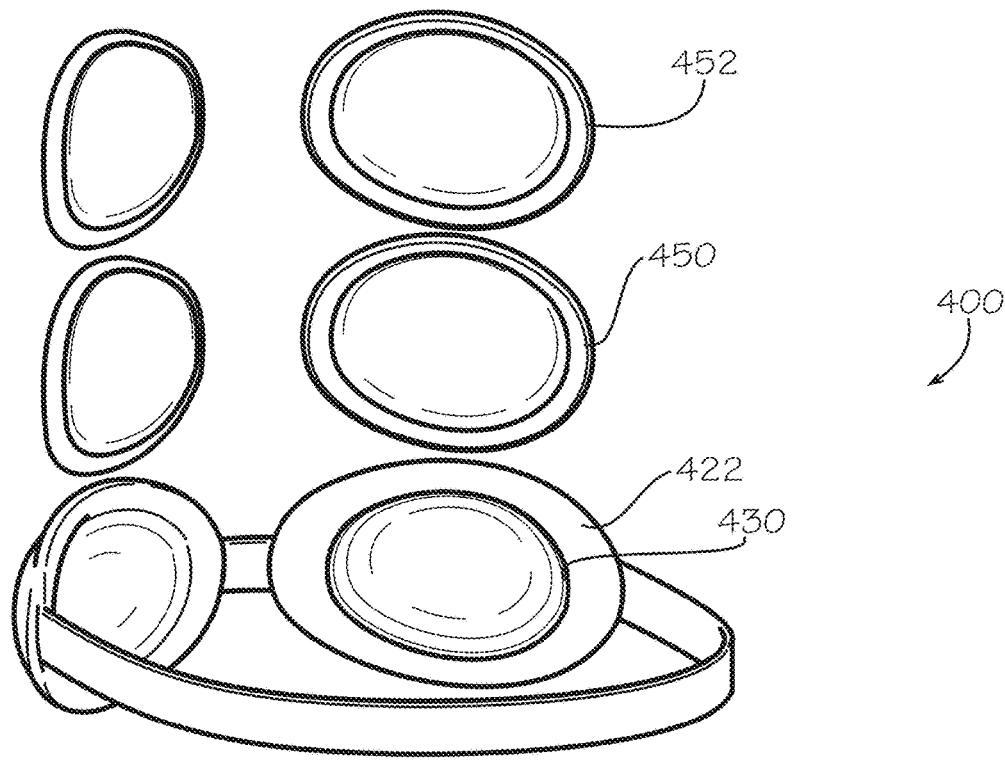
FIG. 13 is an exploded view of a therapeutic eye mask system according to another example embodiment of the invention, having interchangeable pods.

In alternative embodiments, the therapeutic eye mask system 400 may be combined with a heat-transmissive pad or lid scrub or disc 452 that is applied to the skin surface on the eyelid and around the eye, as shown in FIG. 13. In example embodiments, the pad or disc is constructed of a non-woven material and optionally a material that can be RF or thermally sealed to hold an antibacterial or other medication. The pad or disc 452 can be impregnated with medication and can be effective in either a moist or dry condition. The antibacterial medication can include, for example, liposomes and/or microspheres. The pad or disc 452 can be removably secured to the compress for single use or multiple uses. The pad can also be impregnated with materials to improve the aesthetics of the eye, like Vitamin E.

In example embodiments, the medication pad or disc 453 is moist-heat-transmissive, and application of moist-heat activates the release of the impregnated medication from the pad 452 onto the skin surface of the eyelid or other tissue in or around the user's eyes. In example forms, the pad or disc is constructed to prevent the impregnated medication from passing back into the compress during application. For example, a one-way sheet barrier material can be placed between the pad or disc and the compress to prevent any antibacterial medication from the disc from entering the compress.

In example embodiments, the medication pad or disc 452 can have a round or oval disc shape with appropriate size and shape to be placed over a single eyelid or attached to a single eye coverage portion 422. In use, two pads or discs can be used, one attached to each eye coverage portion 422. A plurality of discs can be stored within a container containing antibacterial medication fluid, so as to pre-moisten the discs during storage. In an exemplary manner of use, two discs are removed from the container and one is placed over each eye of a patient while the patient is lying down and the mask is placed over the discs so that the discs are held in between the eye and the eye coverage portion. Alternatively, the disc 452 may be attached to the detachable pod 450, such that when the eye mask or compress is worn, the disc rests in between the eyelid and the detachable pod. In other embodiments, the disc 452 is placed in the receiver 430 with the detachable pod 450.

In other example embodiments, the medicated disc is used as an eyelid cleaning or treatment wipe. The medicated disc is impregnated with a dry specialized formula that is activated by the heat and moisture from the mask. The medication assists in preparing debris in the eye for removal. The disc can then be removed from the mask and used to scrub or wipe the eye area, removing the debris. The disc can be formed of a scrim or non-woven material that accepts dry impregnation of specialized formulas or medication. Ideally, the medicated disc allows the passage of moisture and heat. The medicated disc can remove oil debris and pollen from the eyelids and enhance the moisture of the skin around the eye. The disc can also protect the mask itself from make-up or other contaminants.

Figure 19:
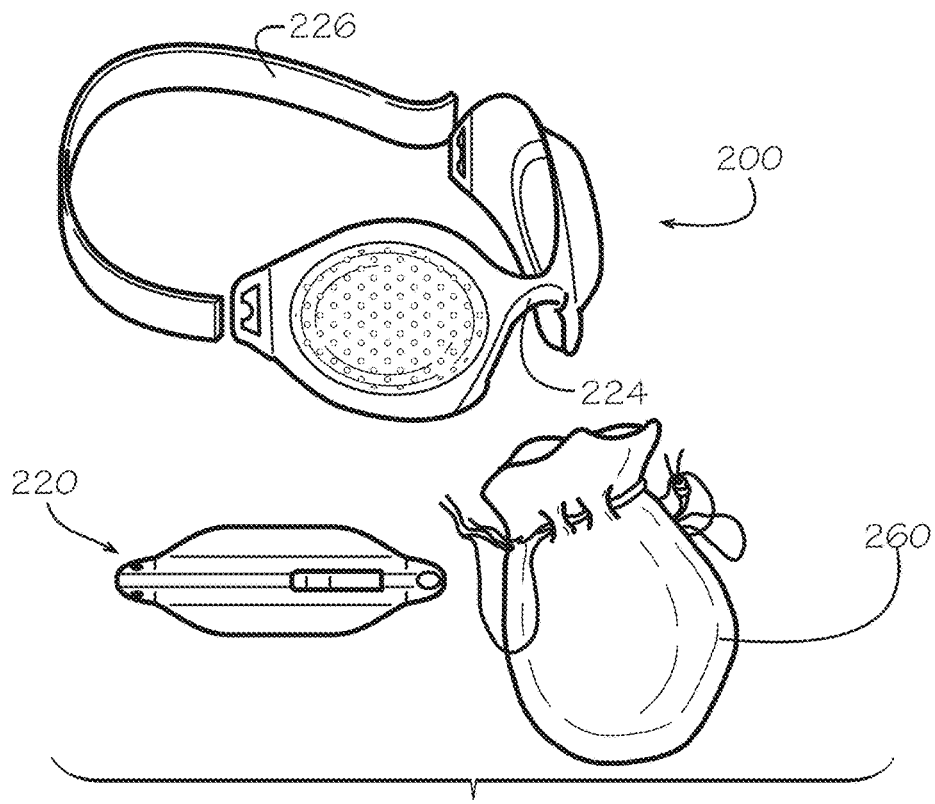
FIG. 19 shows a therapeutic eye mask system according to an example embodiment of the invention.
Figure 20:
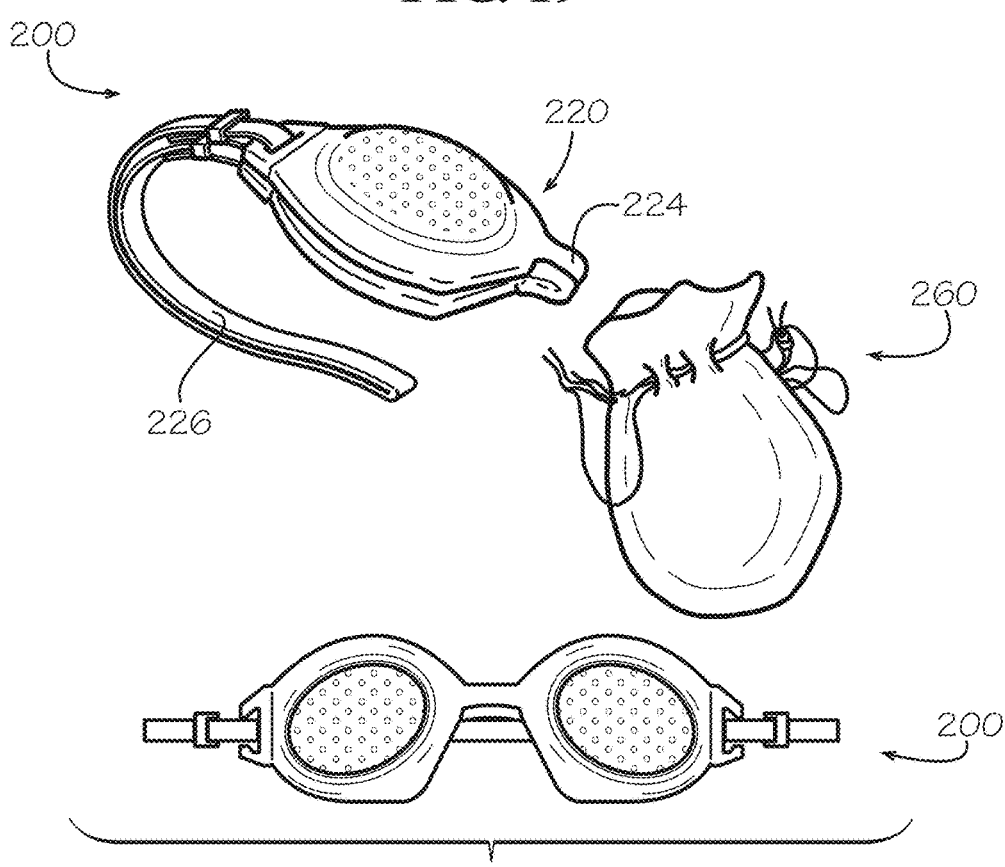
FIG. 20 shows a therapeutic eye mask system according to an example embodiment of the invention.
Figure 21:
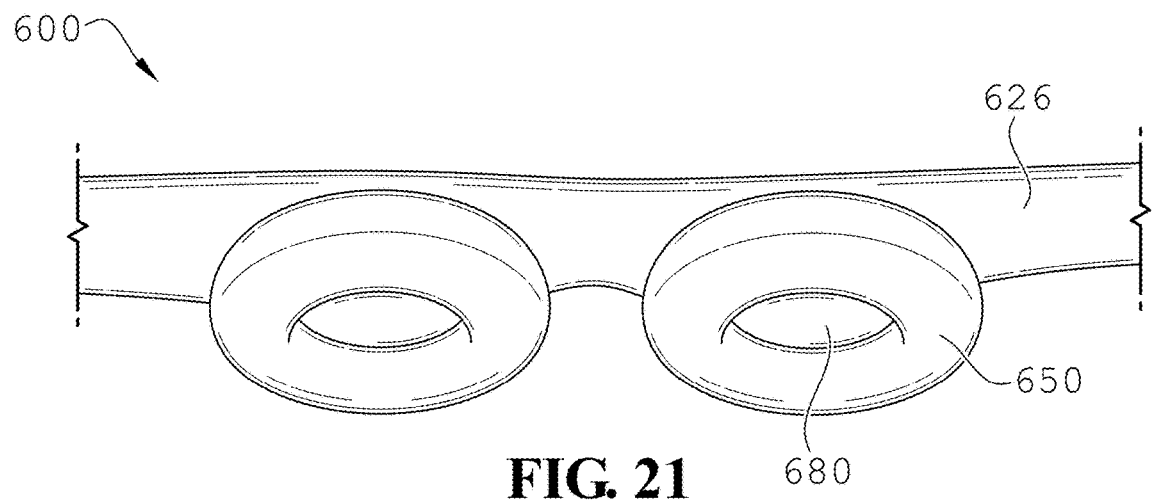
FIG. 21 is a perspective view of a therapeutic eye mask system according to another example embodiment of the invention.
Figure 22:
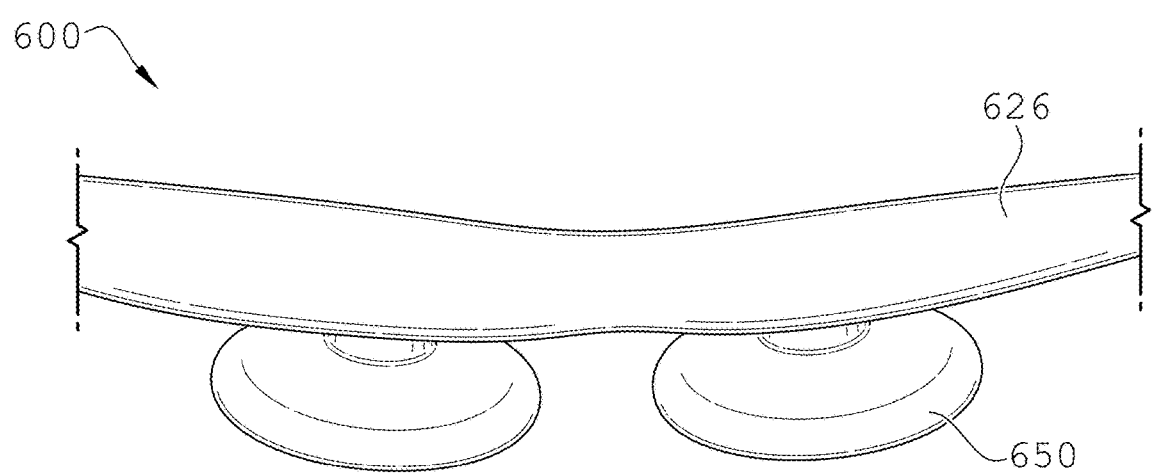
FIG. 22 shows a side view of the therapeutic eye mask system of FIG. 21.

The therapeutic eye mask system 200 can also include a storage bag 260, as shown in FIGS. 19 and 20. In the depicted embodiment the mask portion 220 is configured to fold at the flexible nose bridge 224 to fit within the storage bag 260. The securing strap 226 can be detached from the mask 220 for storage, as shown in FIG. 19, or the mask 220 can be stored with the securing strap 226 attached, as shown in FIG. 20.

Figure 23:
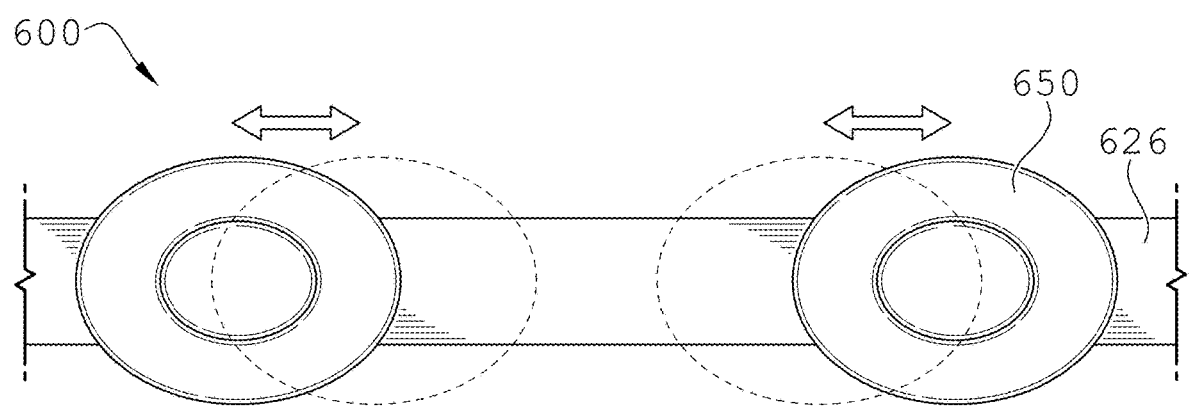
FIG. 23 shows a back view of the therapeutic eye mask system of FIG. 21.
Figure 24:
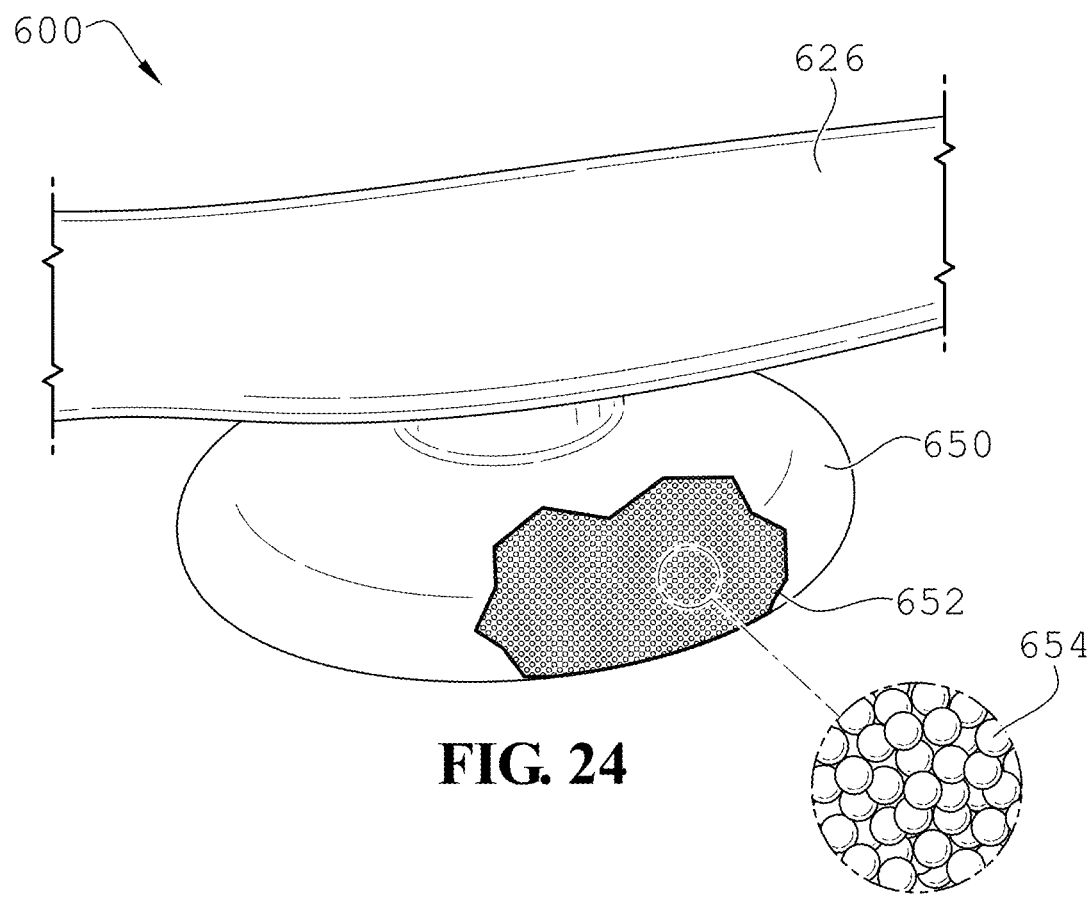
FIG. 24 is a cut-away view of a pod of the therapeutic eye mask system of FIG. 21.

FIGS. 21-24 show a therapeutic eye mask system 600 according to another example embodiment of the invention. The eye mask system 600 generally includes a mask portion or strap 626 and one or more pods 650 that are detachably secured to the strap. In this embodiment, the pods 650 are attached directly to the strap 626 without the need for a receiver as in previous embodiments. The strap 626 is positioned around the user's head to hold the pods 650 in contact with the eye area of the user. The pods 650 are releasably attached to the strap 626 using an attachment mechanism such as snaps, ties, hook-and-loop fasteners or other releasable attachment mechanisms. The pods 650 are attached directly to the strap 626 such that the back side of each pod directly contacts the front of the strap. The front of each pod 650 faces away from the strap 626 and is configured for contact with the eye area of the patient. In example embodiments, the pods 650 can be attached at a plurality of points along the strap 626, as shown in FIG. 23, such that the user can adjust the pods to fit their unique face shape. The pods 650 can also be used independently of the strap 626.

The pods 650 can also include a divot, recess, depression, or other void 680 configured to be positioned over the wearer's corneas when the mask is worn. As explained above, high temperatures may be unsafe for the cornea and the divot or recess 580 positioned over and around the cornea can help prevent the application of excess heat on and around the cornea, preventing conditions such as corneal warping, while allowing heat therapy to reach the eyelid and surrounding eye area.

As in previous embodiments, the pods 650 comprise an outer shell 652 that surrounds and contains a fill material 654. The pod shell 652 is formed from a flexible material such as a fabric. In example embodiments, the pod shell 652 is formed, in whole or in part, from a material with antimicrobial properties. The pod shell 652 material can incorporate an antimicrobial substance, such as silver or other antimicrobial metals. In example embodiments, silver salts or particles are attached to the pod shell fabric. In other embodiments, silver salts or particles are incorporated into fabric fibers such as polyester fibers. The silver particles are encapsulated by the plastic which protects them during manufacturing and use of the mask. The silver impregnated yarn is woven into the fabric of the pod shell 652. The silver impregnated yarn helps ensure that the antimicrobial silver particles are distributed throughout the pod shell 652. The mask can maintain its antimicrobial properties through repeated uses and launderings. The antimicrobial material is configured to kill bacteria in and around the user's eye by contact. In example embodiments, the antimicrobial material will kill 99% of bacteria after 4 hours of contact. In example embodiments, the section of the pod shell 652 that contacts the user's face includes the antimicrobial fibers. In other embodiments, the entire pod shell 652 is formed from a material incorporating antimicrobial fibers. In example embodiments, other components of the mask, such as the strap, are also formed from an antimicrobial material as described above.

The fill material 654 generally comprises a plurality of fill beads or granules. The fill material 654 is contained by the pod shell 652 such that it remains within the shell and does not fall out. The fill material 654 is generally able to move within the pod shell 652 such that the shape of the pod 650 will conform to the face of the user. In example embodiments, the fill beads or granules 654 can be formed from a resilient, deformable material, such as silicon. The resilient, deformable fill beads contribute to the comfort of the user.

Figure 25:
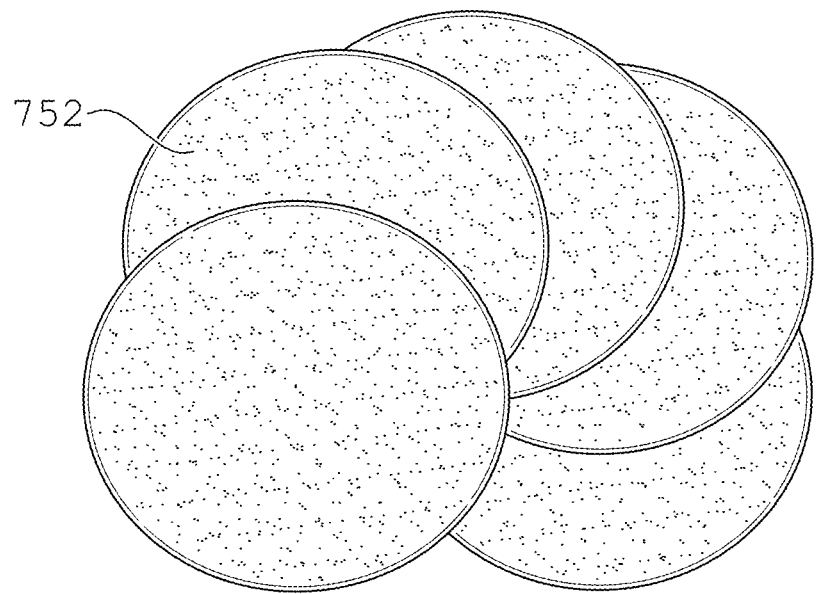
FIG. 25 shows heat-transmissive pads for use with a therapeutic eye mask.
Figure 26:
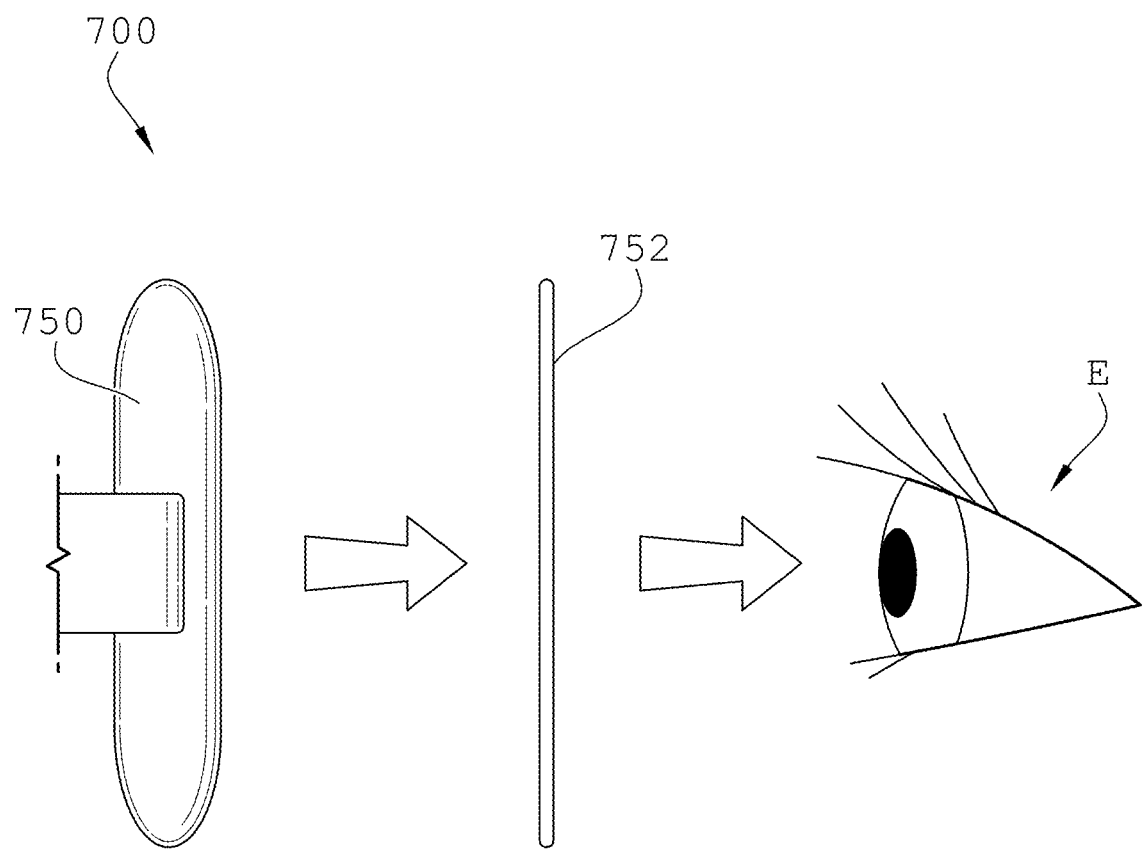
FIG. 26 shows a side exploded view of a therapeutic eye mask system with heat-transmissive pads.

FIGS. 25-26 show a therapeutic eye mask system 700 according to another example embodiment of the invention. The mask system 700 includes a therapeutic mask similar to those described above. The mask system 700 also includes a treatment sheet 752 that can be placed between the eye E of the user and the pod 750 or eye coverage portion. The treatment sheet 752 is generally impregnated with a unique therapeutic formula designed for a specific treatment of the eye area E of a patient. In example embodiments, the treatment sheet 752 is heat-transmissive, such that when the treatment sheet is heated or exposed to a heat source, the impregnated medication is released from the sheet and is able to travel to the eye area of the patient. The treatment sheets can be dry when impregnated with medication. These treatment sheets or pads can be used with a dry heat source. These treatment sheets 752 do not have to be stored in an air-tight container to prevent drying out. These treatment sheets also can be used without having to wet the sheet prior to use.

In example embodiments, the treatment sheets 752 can be a heat-transmissive pad or lid scrub or disc that is applied to the skin surface on the eyelid and around the eye E. The pad or disc 752 can be constructed of non-woven material and optionally a material that can be RF or thermally sealed to hold an antibacterial or other medication. The pads or sheets 752 can be formed from any material that accepts treatment materials and holds them in a dry state until activated by moisture and/or heat. The pad or disc can be impregnated with medication and can be effective in either a moist or dry condition.

In example embodiments, the medication pad or disc is moist-heat-transmissive, and application of moist-heat source activates the release of the impregnated medication onto the skin surface of the eyelid or other tissue in or around the user's eyes. In example forms, the pad or disc is constructed to prevent the impregnated medication from passing through the back of the disc away from the treatment area. For example, a one-way sheet barrier material can be placed between the pad or disk and the compress to prevent any antibacterial medication from the disk from entering the compress.

In example embodiments, the treatment pad or disk 752 can have a round or oval shape, as shown in FIG. 25. The treatment disk 752 is generally a size and shape to be placed on over a single eyelid. In use, two pads or disks can be used, one treats each eye. In alternate embodiments, the sheets can be shaped to cover the entire eye treatment area. A plurality of disks can be stored within a container containing antibacterial medication fluid, so as to pre-moisten the disks during storage. In other embodiments, a medication can be sprayed on the treatment pads prior to use.

In an exemplary manner of use, two disks are removed from the container and one is placed over each eye of a patient while the patient is lying down. The disk or sheet is exposed to a heat source, causing the impregnated medication to be released towards the eye. Alternatively, the disk may be detachably or permanently attached to a reusable or disposable compress delivering dry or moist heat, such that when the eye mask or compress is worn, the disk rests in between the eyelid and the detachable pod. The pad or sheet can include a means for attaching the pad to a compress. Attachment means can include an adhesive material or a fastening device such as a hook and loop fastener. In alternate embodiments, the pad or sheet can be activated by another device producing dry or moist heat, such as a humidifier, a steam or water vapor generator, a heating pad, etc.

Examples of medicants or therapeutic materials capable of delivery using the therapeutic device according to example forms of the invention include a jojoba formulation for treatment of the symptoms of dry eye, steroids such as clobetasol propionate, betamethasone dipropionate, amcinonide or loteprednol etabonate for treatments of diseases of the eyelid, such as chatazion, blepharitis or meibomian gland dysfunction. The medicant can include honey, for example, manuka honey. The medicant or medication can include natural oils including coconut or tea tree oils for the treatment of conditions including Blepharitis. The medicant can be an antibacterial medication including, for example, liposomes and/or microspheres. Medicants may also comprise a dietary or nutritional supplement composition comprising an effective amount of omega-3 fatty acids for treatment of dry eye or meibomianitis. Medicants may also comprise tetracycline, corticosteroids, androgens or androgen analogues. The medicant may also comprise a topical treatment to elevate the side effects of chemotherapy, including eyelash loss. The medicant can include menthol configured to stimulate lacrimoation via activation of cold-sensitive primary afferent neurons in the cornea. Repeated use of menthol can induce persistent increases in tear fluid volume and tear film stability in dry eye patients.

In further embodiments, the therapeutic device takes the form of a hygienic cleaning sheet or pad, including a heat-transmissive substrate configured for cleaning away makeup, debris, oils, contaminants or other materials from a user's eyelids, eyelashes, and surrounding tissue. The sheet or pad may be utilized for hygienic cleansing before, during and/or after application of heat. The substrate is optionally dry coated with one or more natural oils or other hygienic cleansing materials such as for example coconut or tea tree oils, manuka or other honey, menthol, and/or vitamin E. The natural oils or other hygienic cleansing materials optionally provide antibacterial or antimicrobial treatment. In example embodiments, the natural oils or other hygienic cleansing materials are dry coated onto/into the substrate, and configured for release from the substrate toward and onto the eyelids and surrounding tissue or other body parts of a human or animal user, upon application of heat (including moist heat) to the therapeutic device and/or the targeted tissue or body part(s). The natural oils or other hygienic cleansing materials are preferably activated to therapeutically effective levels by application of heat (including moist heat) at safe and comfortable temperatures and moisture levels.

Figure 27:
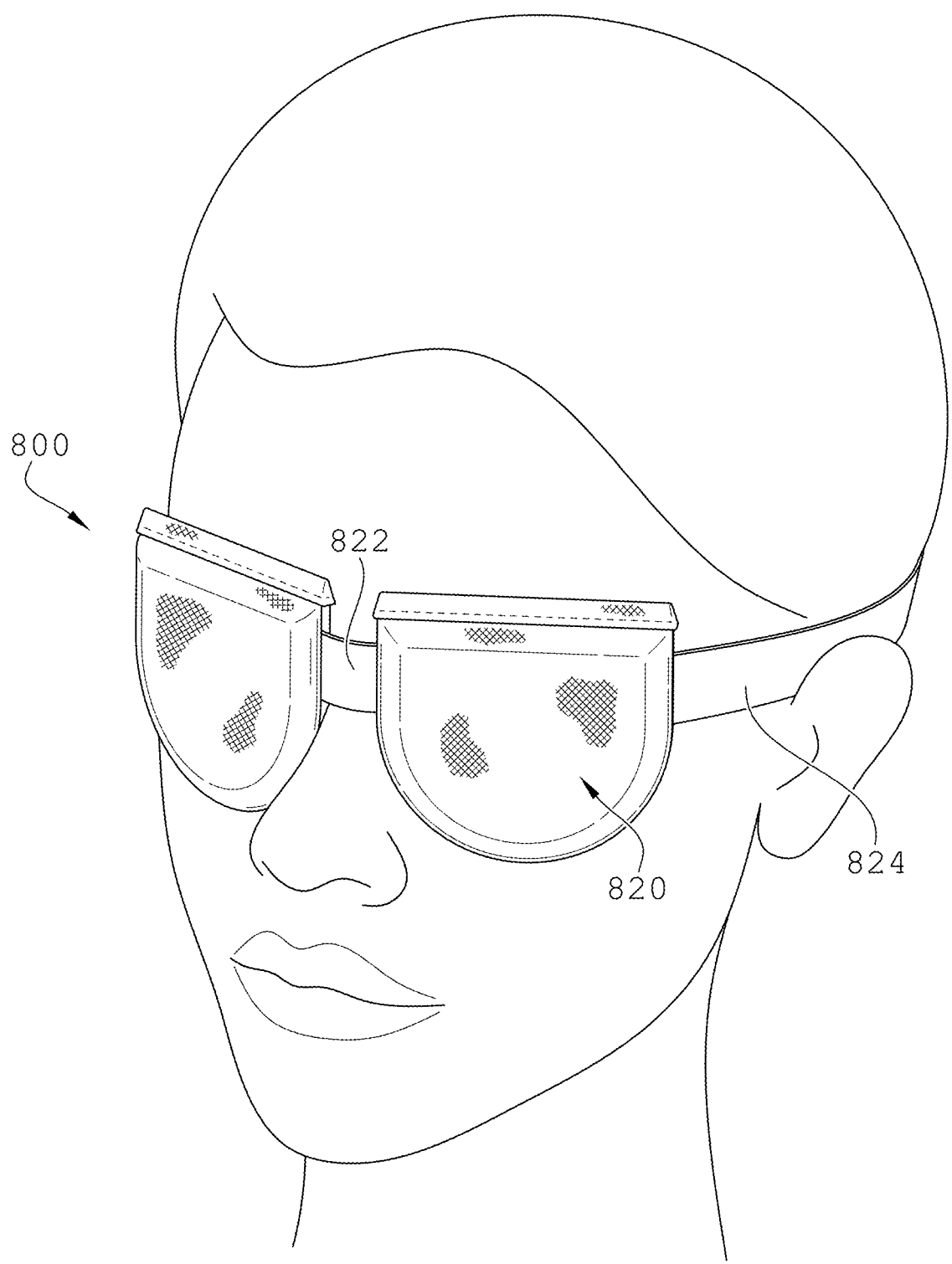
FIG. 27 shows a therapeutic eye mask system according to another example embodiment of the present invention worn by a human patient.
Figure 28:
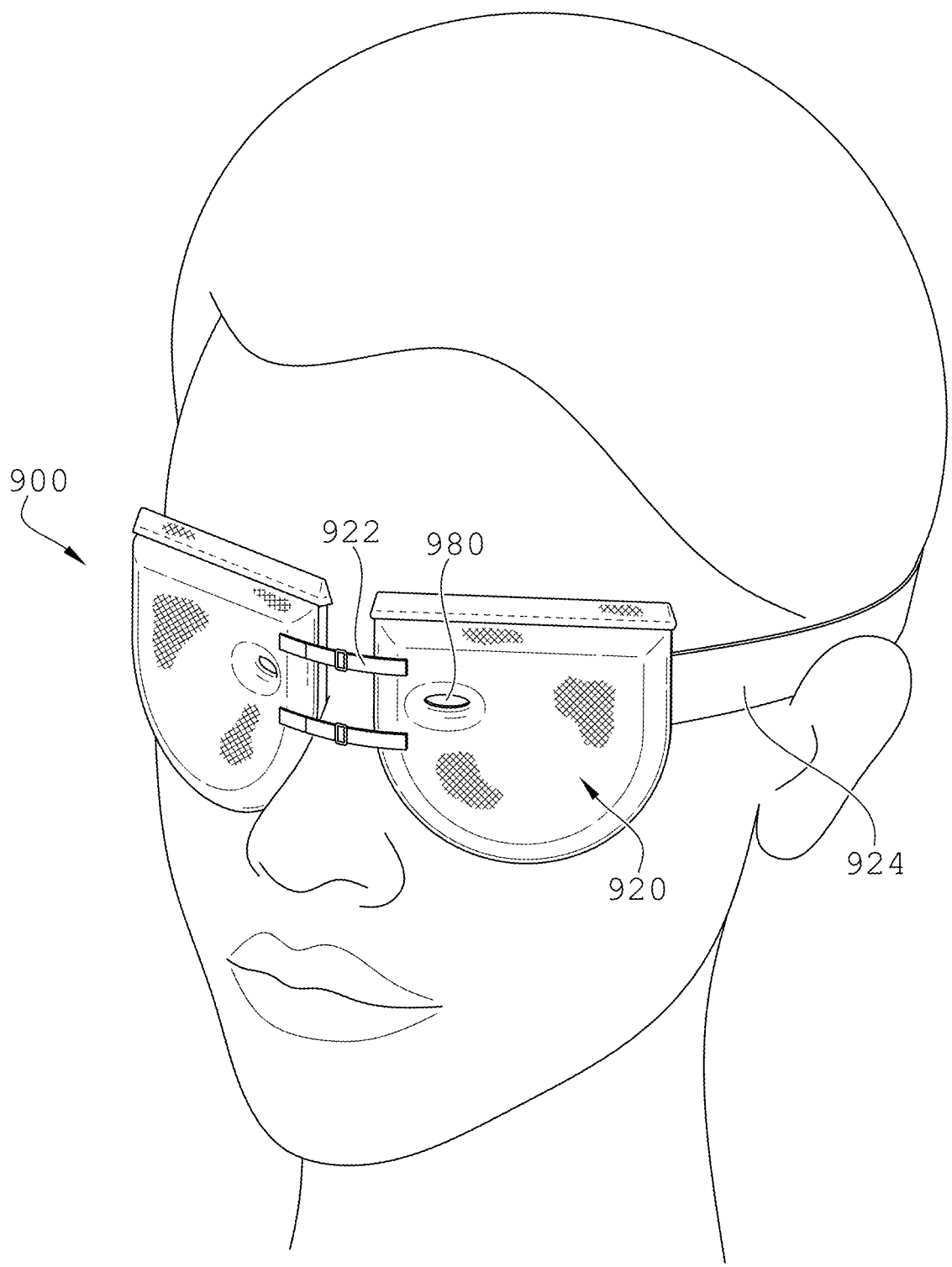
FIG. 28 shows a therapeutic eye mask system according to yet another example embodiment of the present invention.

FIG. 27 shows a therapeutic eye mask or compress 800 according to another example embodiment of the present invention. The mask 800 generally includes at least one, and in the depicted embodiment two separate eye coverage portions 820, each configured to be positioned over the user's eyes when the mask is worn and deliver moist heat therapy. The eye coverage portions are connected by a flexible nose bridge 822 and a securing strap or head band 824, as shown in FIG. 27. In example embodiments, the nose bridge 822 and/or securing strap 824 may comprise a flexible elastic material or strip, and optionally also comprise one or more attachment or the like, to allow attachment and optionally also comprise one or more attachments or connection elements such as hook-and-loop attachment material, snaps, clips, buttons or the like to allow attachment and optionally adjustment of the fit around the user's head. The mask 800 is configured to be worn on the head of a human or animal patient with one of the eye coverage portions 820 against or adjacent over the eyes of the user, as shown in FIG. 27. In alternate embodiments, a mask or compress having a single eye coverage potion is provided, allowing the user to treat one eye at a time, leaving the other eye uncovered.

FIGS. 28-31 show a mask 900 according to another example embodiment of the present invention. In the depicted embodiment, each eye coverage portion 920 includes an opening, recess, depression, slit or another void 980 configured to be positioned over the wearer's corneas when the mask is worn. Temperatures over 39.5° Celsius may be unsafe for the cornea. The openings or voids 980 positioned over and around the cornea can help prevent the application of excess heat on and around the cornea, preventing conditions such as corneal warping, while allowing moist heat therapy to reach the eyelid and surrounding eye area. In example embodiments, the cornea voids 980 are around 15 mm wide. In example embodiments, the voids 980 can be recessed in the eye coverage portion 920 or detachable pods or alternatively can be slits or openings extending through the entire thickness of the eye coverage portion and detachable pods whereby the user can see through the openings when worn. In alternate embodiments, the eye coverage portions or detachable pods can include a heat insulating material applied over one or more portions of the eye covers configured to be positioned over the corneas when in use. For example, an insulating shield can be attached to the central regions of each eye cover 920 or detachable pod. The insulating shield is configured to vault the cornea and prevent the application of excess heat on or around the corneas. This embodiment can further include an adjustable, flexible nose bridge 922. The adjustable nose bridge 922 allows the user to adjust the spacing distance between eye coverage portions 920 and/or between the voids in each eye cover to accommodate varying distances between human eyes from one individual to the next. The average pupillary distance for a human is around 57 mm to 65 mm. In example embodiments, the adjustable nose bridge 922 can be changed to accommodate a distance between cornea areas ranging from about 45 millimeters to about 74 millimeters. This range is sufficient to accommodate the eye placement of the majority of adult and/or child male and female humans. In example embodiments, one or more adjustable or expandable straps or bands are provided between the eye covers to allow adjustment of the relative positions or spacing of the eye covers. Alternatively, the eye covers can be detachably mounted to the retention strap, for example with hook-and-loop fastener material, to allow for repositioning of the eye covers on the strap to vary the spacing and position of the eye covers.

Figure 32:
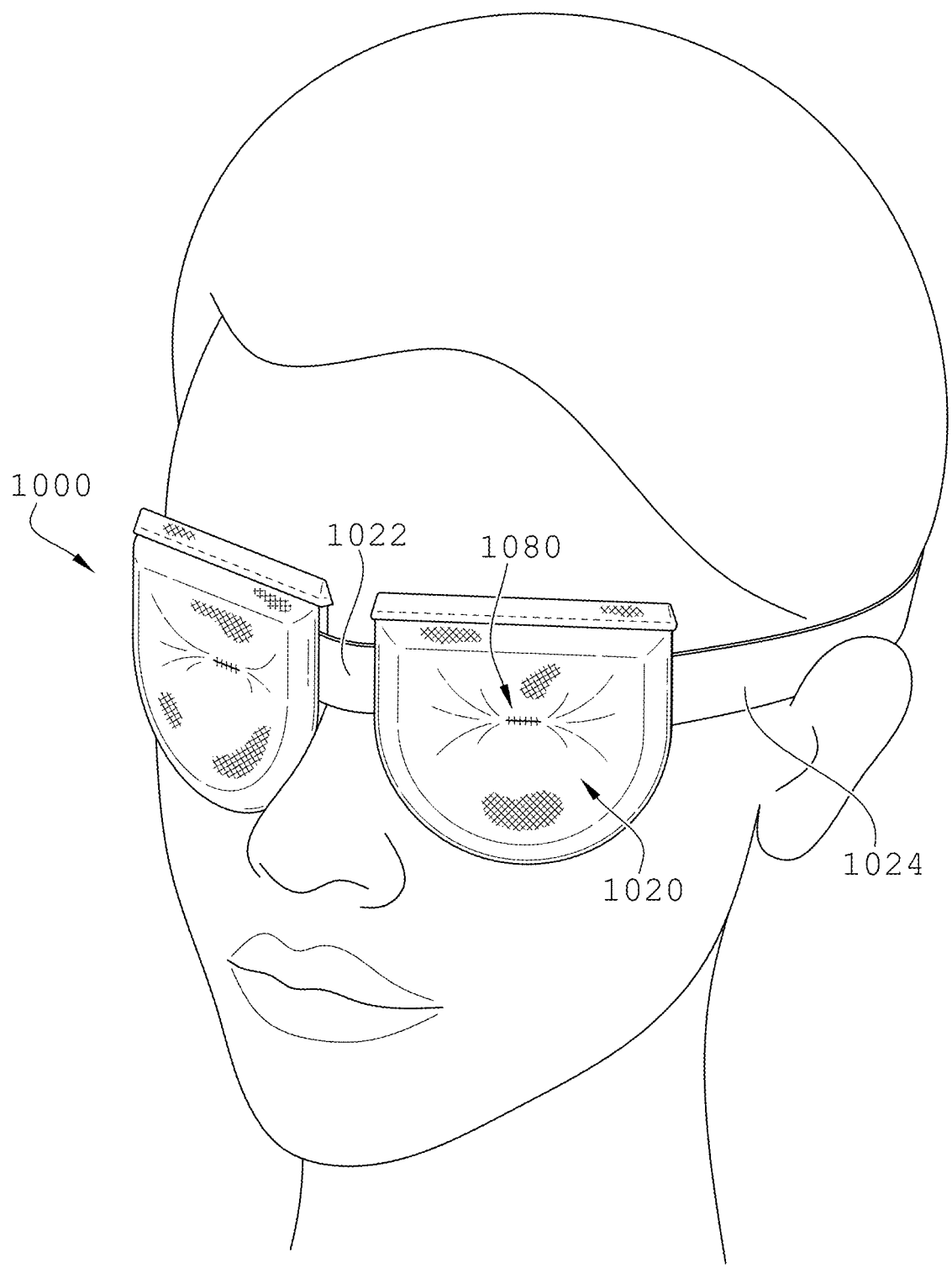
FIG. 32 shows a therapeutic eye mask system according to another example embodiment of the present invention.

FIGS. 32-34 show a therapeutic eye mask or compress 1000 according to another example embodiment of the present invention. The therapeutic eye mask 1000 generally includes at least one, and in the depicted embodiment two separate eye coverage portions 1020, each configured to deliver moist heat therapy to the eye regions of the user, connected by a nose bridge 1022 and a securing strap 1024 for placement around the user's head to hold the compress 1000 in place, as shown in FIG. 32-33. In example embodiments, the nose bridge 1022 and/or the securing strap 1024 may comprise a flexible elastic material or strip, and optionally also comprise one or more attachment or connection elements such as hook-and-loop attachment material, snaps, clips, buttons or the like, to allow attachment and optionally adjustment of the fit around the user's head. One or more size-adjustment connections are optionally provided to allow the user to fit the compress 1000 to their head and eye regions. The mask 1000 is configured to be worn on the head of a human or animal patient with one of the eye coverage portions 1020 positioned over a respective eye of the patient. In example embodiments, the securing strap 1024 is positioned around the user's head to hold the eye coverage portions 1020 against or adjacent over the eyes of the user, as shown in FIG. 32. In alternate embodiments, a mask or compress having a single eye coverage portion is provided, allowing the user to treat one eye at a time, leaving the other eye uncovered, or a larger mask configured to cover both eyes may be provided.

Each eye coverage portion 1020 has an inner front face or application side 1070, configured to rest against the face of the patient (the inner or patient treatment side of the compress), and an outer back face or distal side 1060 opposite the front face (the outer or distal side of the compress). In example embodiments, the inner or front face 1070 of the eye coverage portion 1020 has a different appearance and/or texture than the outer or back side 1060, to allow a user to readily differentiate which side of the compress is the patient treatment side to be applied over and against the patient's eye region. For example, the inner or front side 1070 may comprise a smoother or softer material without coloration or printing, whereas the outer or back side 1060 may comprise a more durable or rougher textured material having branding text or logos, or other coloration or indicia imprinted or otherwise applied thereon. Alternatively, instructional information may be imprinted or otherwise applied on one or both sides (for example, "this side toward you" printed on the inner or front side).

In the depicted embodiment, each eye coverage portion 1020 also includes a recess or depression 1080 created by a segment of stitching, suture or other means of attachment between the inner face 1070 and the outer face 1060, forming a pinched or retracted central region in each eye coverage portion. The recess 1080 is configured to be positioned over the center of the wearer's eye to protect the wearer's corneas from excess heat and/or to provide improved comfort when the mask is worn. Temperatures over 39.5° Celsius may be unsafe for the cornea. The recesses 1080 are positioned over and around the cornea to provide a localized non-contact or lesser contact area to help prevent the application of excess heat on and around the cornea, preventing conditions such as corneal warping, while allowing moist heat therapy to reach the eyelid and surrounding eye area. In example embodiments, the recess or depression 1080 is formed in at least the inner or front side 1070 of the eye coverage portion(s), and optionally in both the inner side 1070 and the outer side 1060 as depicted. In example embodiments, the stitched segments 1080 are about 5-15 mm wide, and preferably about 8-12 mm wide, for example about 10 mm wide. In example embodiments, the recessed regions 1080 are formed by sewing a thread through both the inner and outer face panels 1070, 1060, or alternatively by adhesive attachment, thermal bonding, staple, clip or other attachment or coupling means. In example embodiments, the stitched recesses 1080 can be formed in the eye coverage portions 1020 as depicted or in detachable pods as described elsewhere herein.

As in previous embodiments, the eye coverage portions 1020 comprise an outer fabric shell that surrounds and contains a loose granular or particulate fill material 1040. The shell is formed from a flexible material such as a knitted or woven fabric. In example embodiments, the shell is formed, in whole or in part, from a material with antimicrobial properties. For example, the shell material can incorporate an antimicrobial substance, such as silver or other antimicrobial metals. In example embodiments, silver salts, fibers or particles are attached to or embedded or woven within the eye coverage shell fabric. In other embodiments, silver salts or particles are incorporated into fabric fibers such as polyester fibers. The silver particles are optionally encapsulated by the fiber material which protects them during manufacturing and use of the mask. In example embodiments a silver impregnated yarn is woven into the fabric of the shell. The silver impregnated yarn helps ensure that the antimicrobial silver particles are distributed throughout the eye coverage portion shell. The mask can maintain its antimicrobial properties through repeated uses and laundering. The antimicrobial material may be configured to kill bacteria and pathogens in and around the user's eye by contact. In example embodiments, the antimicrobial material will kill 99% of bacteria after 4 hours of contact. In example embodiments, the section of eye coverage portion 1020 that contacts the user's face includes the antimicrobial fibers. In some embodiments, the entire eye coverage portion 1020 is formed from a material incorporating antimicrobial fibers. In particular example embodiments, the shell fabric comprises 5-15% elastic fabric, 25-35% material with antimicrobial properties, and 50-70% regular fiber, including but not limited to cotton, polyester, wool, silk, and flax, and/or combinations thereof. In further embodiments, the shell fabric is formed from about 10% elastic fabric, about 30% material with antimicrobial properties, and about 60% regular fiber. In example embodiments, the material incorporating antimicrobial properties may comprise a PurThread® material and the elastic material may comprise Lyrcra®. In example embodiments, other components of the mask, such as the strap, are also formed from an antimicrobial material as described above.

The fill material 1040 generally comprises a plurality of fill beads or granules. The fill material 1040 is contained within each eye coverage portion 1020 such that it remains within the shell and does not fall out. The fill material 1020 is generally able to flow or move within the eye coverage portions such that the shape of the coverage portion 1020 will conform to the face of the user. In example embodiments, the fill beads or granules 1020 can be formed from a resilient, deformable material, such as silicon. The resilient, deformable fill beads contribute to the comfort of the user. In example embodiments, the fill material 1040 contained within the eye coverage portion 1020 comprises a synthetic porous crystalline granular aluminosilicate zeolite, for example, a hydrophilic natural or synthetic zeolite, as previously disclosed herein.

Figure 35:
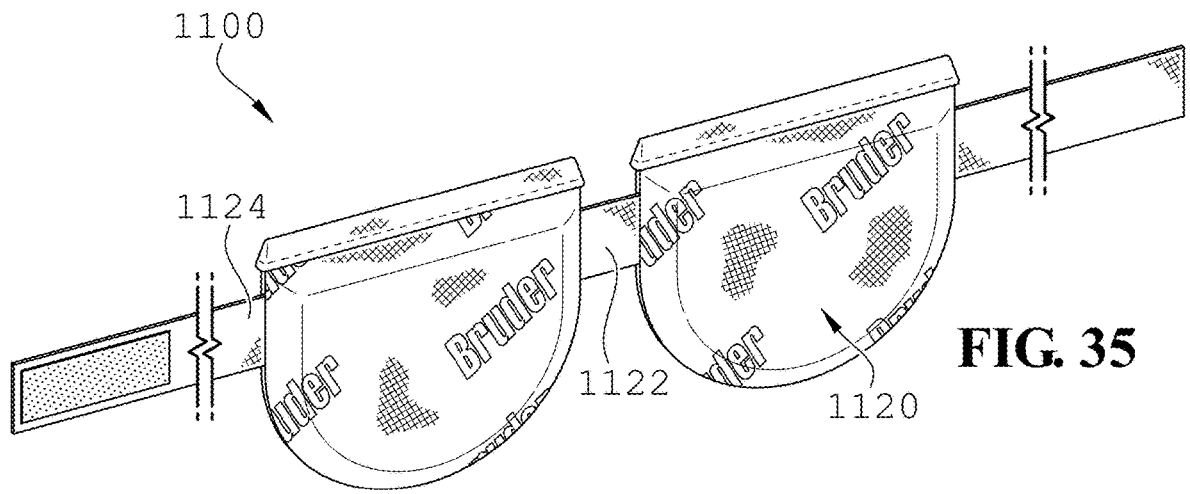
FIG. 35 is a perspective view of a therapeutic eye mask according to another example embodiment of the present invention.
Figure 36:
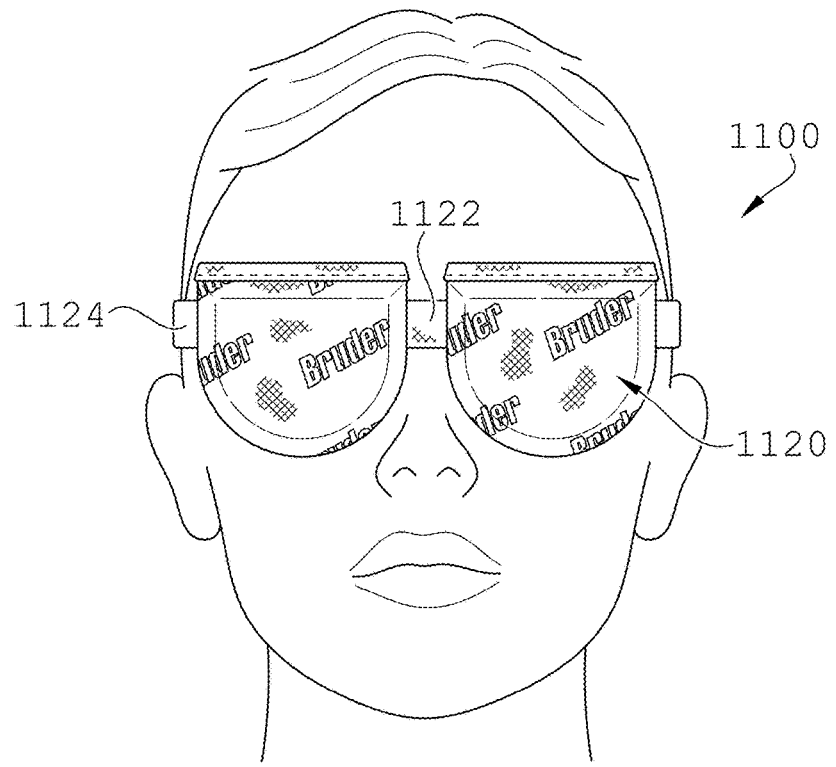
FIG. 36 shows the therapeutic eye mask of FIG. 35 worn by a human patient.
Figure 37:
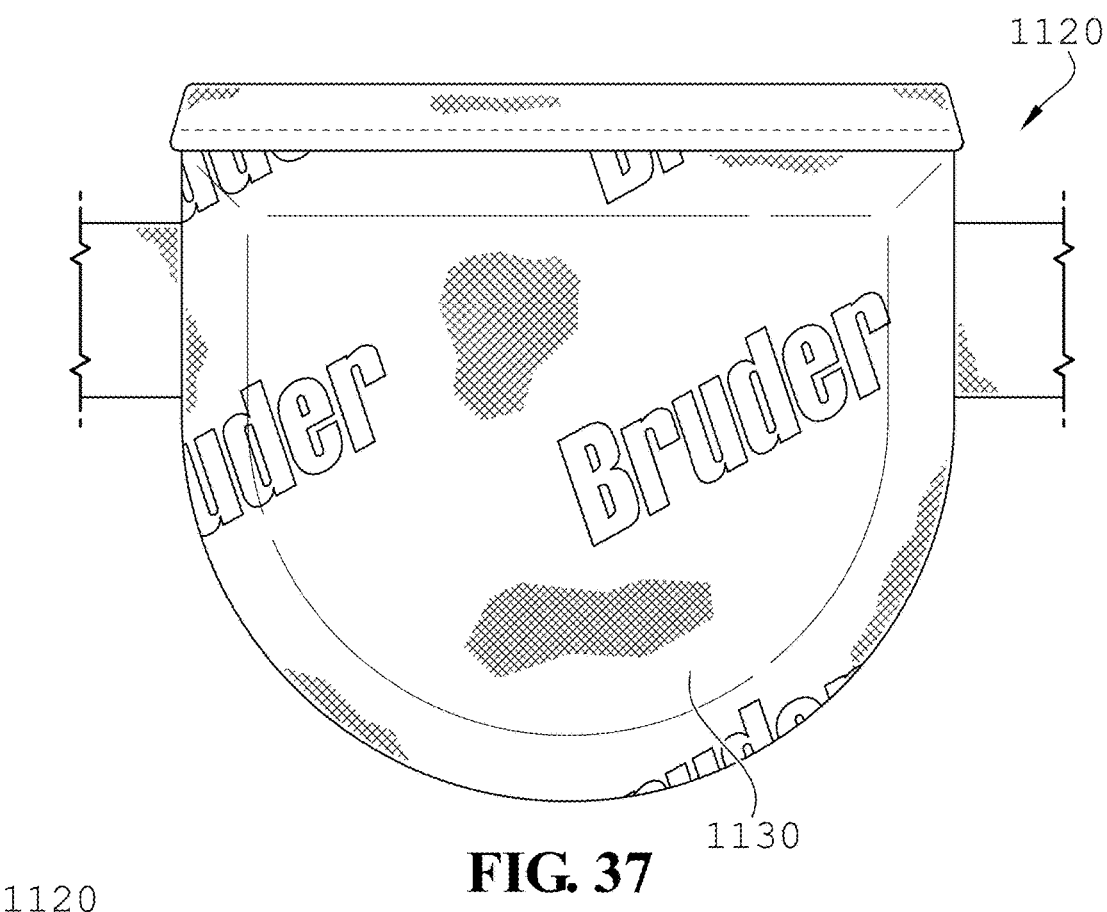
FIG. 37 is a detailed view of the back side of an eye coverage portion of the therapeutic eye mask of FIG. 35.

FIGS. 35-42 show a therapeutic eye mask or compress according to an example embodiment of the present invention. The therapeutic eye mask 1100 generally includes at least one, and in the depicted embodiment two separate eye coverage portions 1120, each configured to deliver moist heat therapy, connected by a nose bridge 1122 and a securing strap 1124, as shown in FIG. 35. In example embodiments, the nose bridge 1122 and/or the securing strap 1124 may comprise a flexible elastic material or strip, and optionally also comprise one or more attachment or connection elements such as hook-and-loop attachment material, snaps, clips, buttons or the like, to allow attachment and optionally adjustment of the fit around the user's head. The mask 1100 is configured to be worn on the head of a human or animal patient with one of the eye coverage portions 1120 positioned over each eye of the patient. In example embodiments, the securing strap 1124 is positioned around the user's head to hold the eye coverage portions 1120 against or adjacent over the eyes of the user, as shown in FIG. 36. In alternate embodiments, a mask or compress having a single eye coverage portion is provided, allowing the user to treat one eye at a time, leaving the other eye uncovered. Each eye coverage portion 1120 has a front side or end 1126, configured to rest against the face of the patient (the inner or patient treatment side of the compress), and a back side or end 1128 opposite the front side or end (the outer or distal side of the compress). FIG. 37 shows a detailed view of the back side 1128 of an eye coverage portion 1120. In example embodiments, the inner or front side 1126 of the eye coverage portion 1120 has a different appearance and/or texture than the outer or back side 1128, to allow a user to readily differentiate which side of the compress is the patient treatment side to be applied over the patient's eye region. For example, the inner or front side may comprise a smoother or softer material without coloration or printing, whereas the outer or back side may comprise a more durable or rougher textured material having branding text or logos, or other coloration or indicia imprinted or otherwise applied thereon. Alternatively, instructional information may be imprinted or otherwise applied on one or both sides (for example, "this side toward you" printed on the inner or front side). Each eye coverage portion 1120 includes a moisture barrier material 1134, positioned towards the back or outer side 1128 of the eye coverage portion, configured to prevent moisture from escaping from the back or outer side of the eye coverage portion, thereby directing moist heat therapy toward the front or inner side for application to the eye region of the patient (i.e., in a patient-treatment direction).

Figure 38:
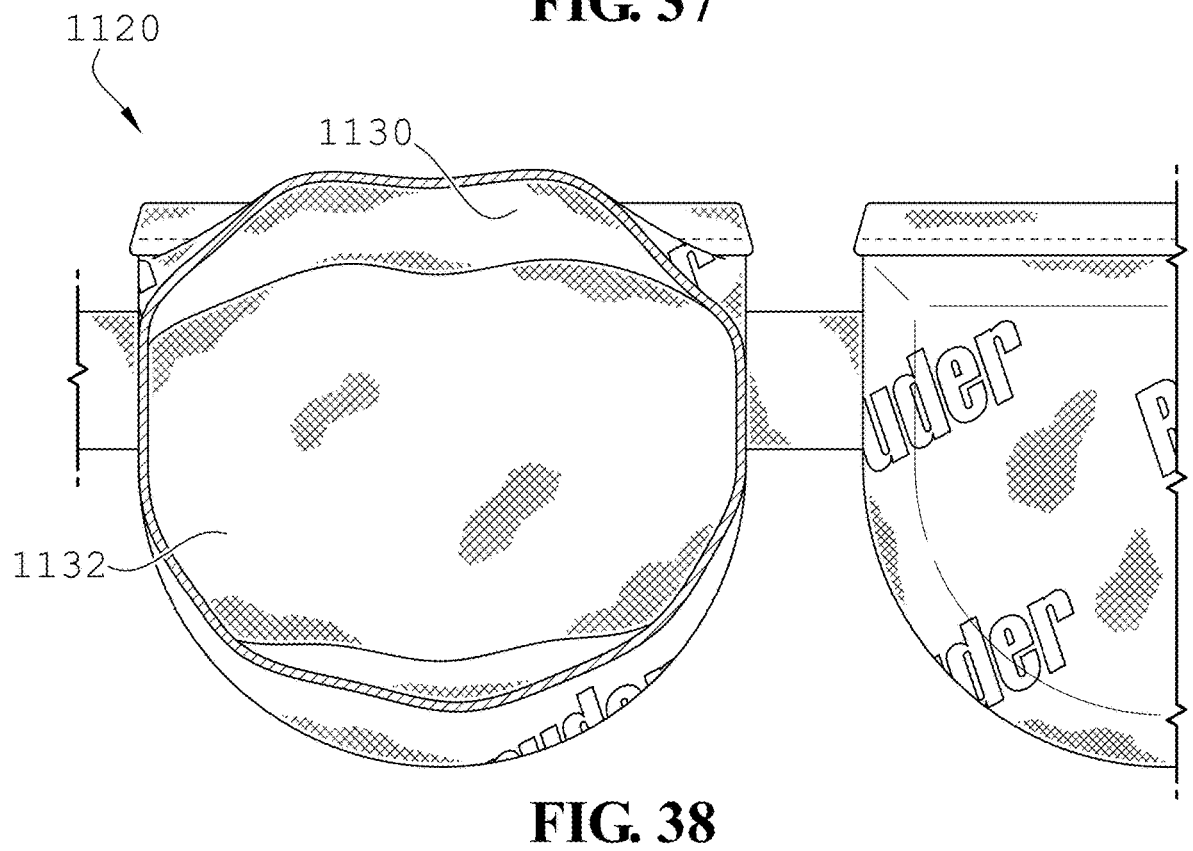
FIG. 38 is a cutaway view of the eye coverage portion of FIG. 37, wherein the outer cover layer is retracted.
Figure 39:
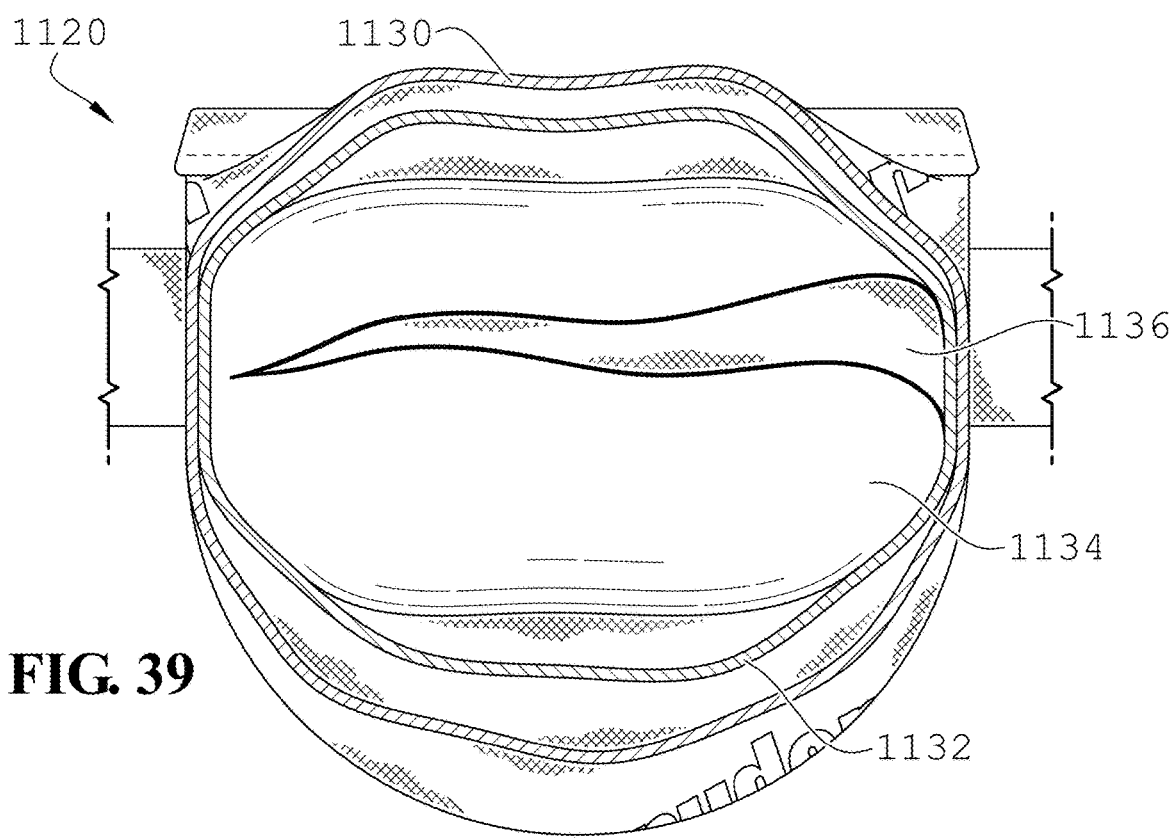
FIG. 39 is a cutaway view of the eye coverage portion of FIG. 37, wherein the outer cover layer and intermediate layers are retracted.
Figure 40:
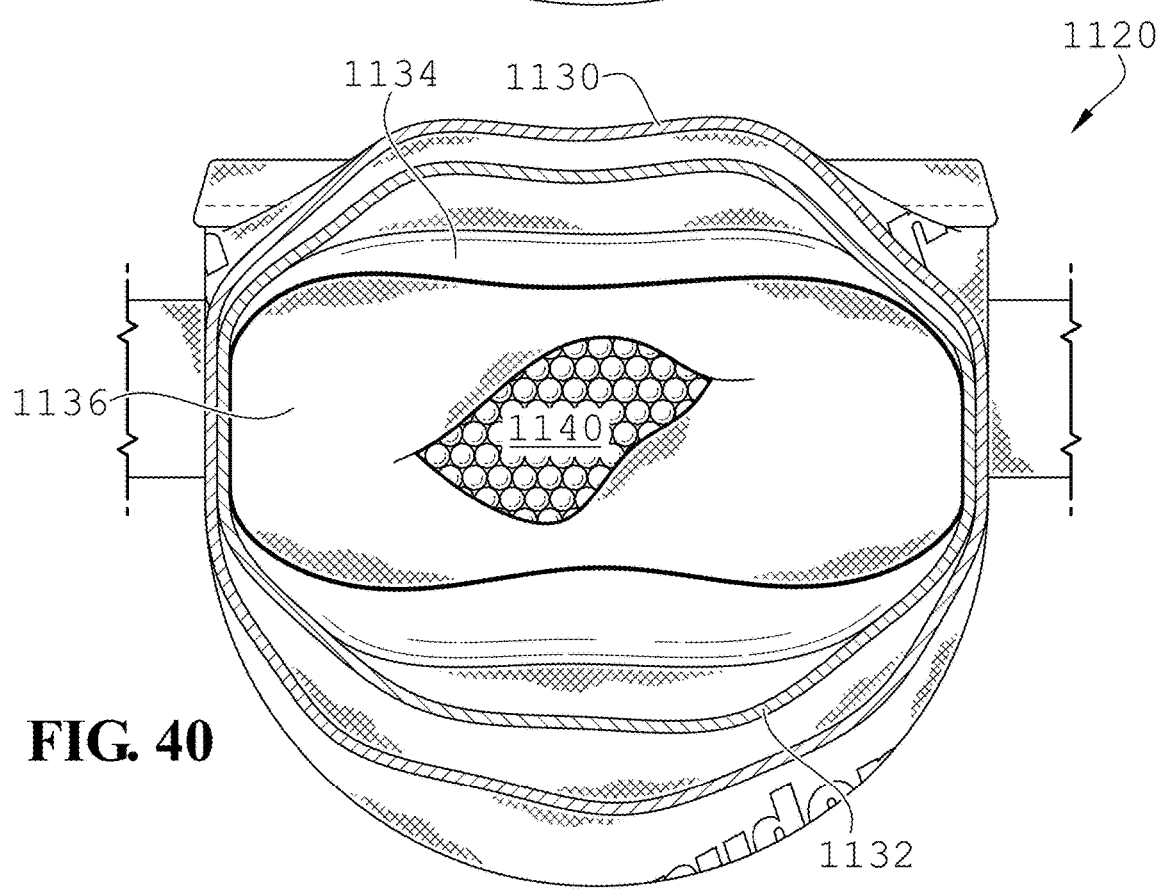
FIG. 40 is a cutaway view of the eye coverage portion of FIG. 37, wherein the outer cover layer, intermediate layer, the moisture impermeable panel, and the inner pouch are retracted.
Figure 41:
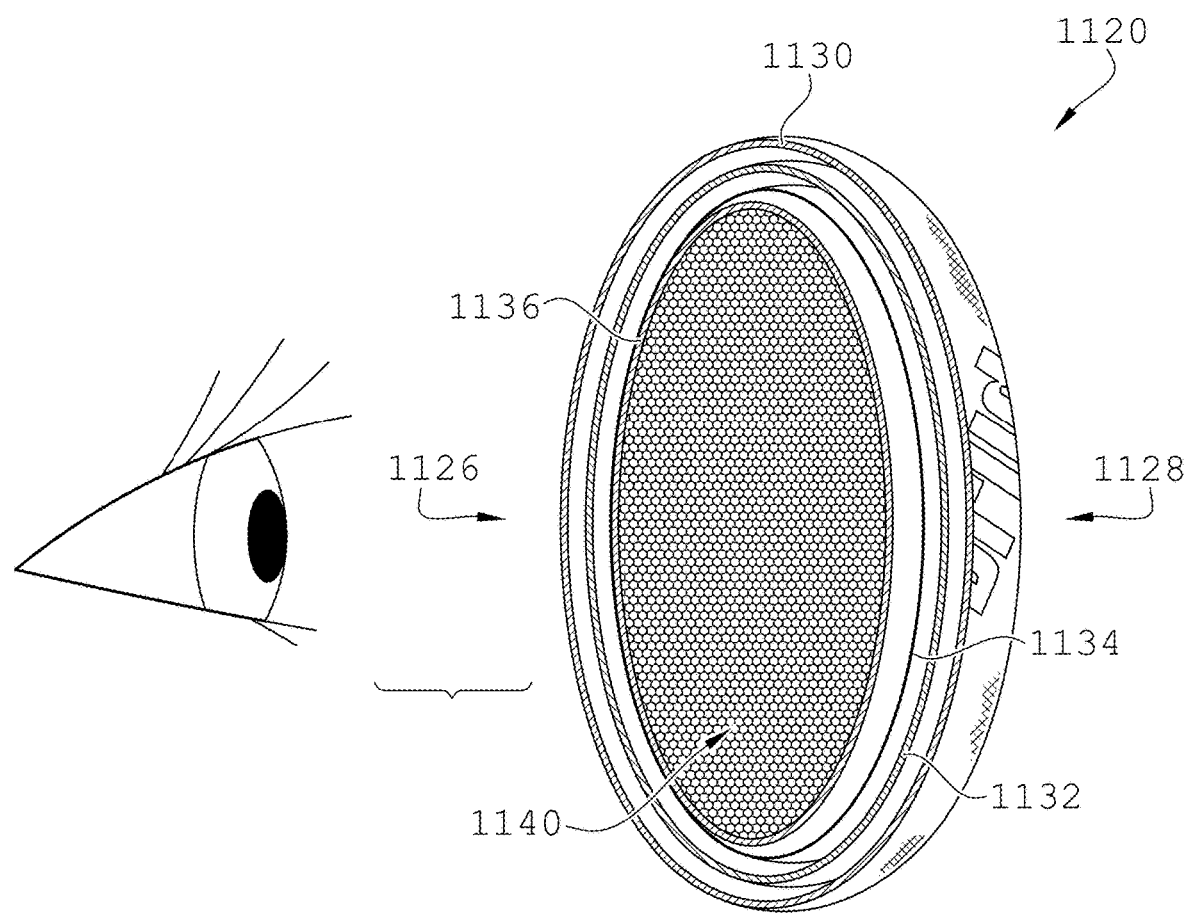
FIG. 41 is a partial cross-section of an eye coverage portion of the therapeutic eye mask of FIG. 35.
Figure 42:
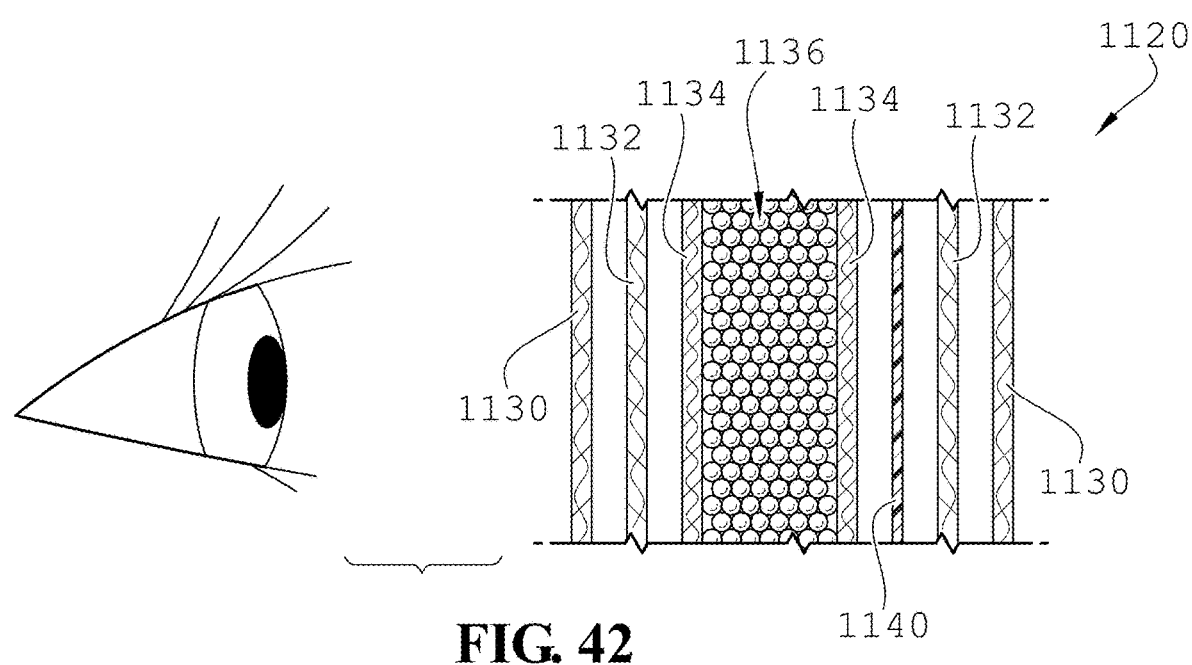
FIG. 42 shows a detailed cross-section of the eye coverage portion of the therapeutic eye mask of FIG. 35.

In example embodiments, the eye coverage portions 1120 are independent structures such that each can independently conform to the respective eye region of the patient. For example, in the depicted embodiment as shown in greater detail in FIG. 37, the eye coverage portion 1120 has a radially curved lower or bottom profile, and a generally rectangular upper or top profile, defining a generally U-shaped configuration. Optionally, an upper attachment strip is stitched along the top edge of the eye coverage portion. Alternatively, the eye coverage portions can be combined in a single panel or mask format configured to extend over both eyes. In the depicted embodiment, each eye cover portion 1120 is formed from a series of layers or lamina. FIGS. 38-40 show successive layers being cut away and retracted to show the series of layers or lamina, and FIG. 41 shows a cross-sectioned view of a portion of an eye cover with the successive layers or lamina indicated. For example, the eye coverage portion 1120 can include an outer cover 1130 configured to surround the eye coverage portion 1120. The outer cover 1130 generally surrounds both the front side 1126 and back side 1128 of the eye coverage portion 1120, as shown in FIG. 41. The eye coverage portion also includes an inner pouch 1136 that holds a fill material 1140, as shown in FIG. 40, configured to retain moisture and deliver moist heat. The outer cover 1130 is configured to surround and contain the inner pouch 1136. The inner pouch 1136 and outer cover 1130 are preferably at least partially moisture permeable such that moisture and heat (moist heat) can travel from the fill material 1140 to the face of the patient. In example embodiments, the eye coverage portion 1120 also includes a panel or sheet 1134 of moisture impermeable or minimally-moisture permeable material. The panel 1134 is positioned between the inner pouch 1136 and the outer cover 1130 of the eye coverage portion 1120. The panel 1134 is generally positioned towards the back or outer side 1128 of the eye coverage portion 1120 such that the panel is not positioned between the inner pouch 1136 and the face of the patient, as shown in FIG. 41. The moisture impermeable panel 1134 is configured to help prevent the moisture released from the fill material 1140 from escaping through the back end 28 of the eye coverage portion 1120, and better direct moist heat to the subject for treatment. In example embodiments, the panel 1134 can be simply held between the outer cover 1130 and the inner pouch 1136. In other embodiments, the panel 1134 can be attached to the outer cover 1130, the inner pouch 1136, or another part of the eye coverage portion. Example attachment means include gluing, sewing, or other fastening means. In other embodiments, the moisture barrier panel 1134 is laminated to another layer of the eye coverage portion to form a unitary structure. The panel 1134 can be flame laminated to eliminate potential for skin contact with any irritant adhesive materials. For example, the panel 1134 can be laminated to the outer rear surface of the inner pouch 1136 or the inner rear surface of the outer cover 1130.

In other embodiments, the eye coverage portions 1120 can include an intermediate layer 1132 in between the inner pouch 1136 and the outer cover 1130, as shown in FIGS. 38 and 39. The intermediate layer 1132 is generally formed from a moisture permeable material. In example embodiments, the intermediate layer 1132 surrounds and contains the inner pouch 1136. In other embodiments, the intermediate layer 1132 covers only a portion of the inner pouch 1136. In these embodiments, the moisture-barrier panel 1134 can be attached or laminated to the inner rear surface or the outer rear surface of the intermediate layer 1132.

In example embodiments, the outer cover 1130, inner pouch 1136, and intermediate layer 1132 are constructed of a lightweight, durable, and flexible material such as foam or polyester. The material is configured to allow moist heat to reach the face of the patient, but limit the amount of moisture released from the fill material. In example embodiments, one or more of the layers 1130/1132/1136 are formed from an open cell thermoplastic polyurethane foam that is about 2 mm thick. In other examples, one or more of the layers 1130/1132/1136 are constructed from a 2 lb/ft3 (pounds per cubic foot), 3/8" thick polyether polyurethane foam. The foam layers can include polyester fabric laminated onto one side. Alternatively, one or more of the layers 1130/1132/1136 are constructed from polyester, rayon, spandex, silk, polyethylene, neoprene, ECA, ethylene-vinyl acetate (EVA), other plastic films, and/or other natural and/or synthetic fabrics or materials having the same or substantially similar characteristics and capabilities. For example, one or more of the layers 1130/1132/1136 can be formed from polyester felt. In other embodiments, one or more of the layers 1130/1132/1136 are formed from a closed cell foam. The foam can be polyurethane and/or thermoformable. The outer cover 1130 can alternatively be constructed from a woven material different from the inner pouch 1136 and intermediate layer 1132. The mask material can optionally be selected to have insulative or heat-transmissive properties to affect the temperature transferred from the mask to the patient's eyes, better ensuring safety. The material may optionally be washable for reuse, or alternatively can be a single-use disposable product. In example embodiments, the eye coverage portions 1120 can be constructed of a material containing nanobeads comprising an antimicrobial metal, medications, and/or other therapeutic material(s). Optionally, the mask 1100 may be configured for use in connection with medicated or therapeutic sheets, pods or other therapeutic accessories positioned or retained between the eye coverage portions 1120 and the subject's eye areas. For example, the mask 1100 may be configured for supplemental delivery and transport of medication or therapeutic material with moist heat.

The moisture barrier panel or material 1134 can be constructed of a flexible material that will limit moisture that may otherwise be lost through the open cell foam, e.g., a plastic material. In example embodiments, the panel 1134 is formed of a multilayer structure of nylon, ethylene vinyl alcohol (EVOH), and polyethylene (PE) that is about 4 mm thick, other plastic films, and/or other natural and/or synthetic fabrics or materials having the same or substantially similar characteristics and capabilities.

In example embodiments, the fill material 1140 is loosely contained within the inner pouch 1136 and comprises a synthetic porous crystalline granular aluminosilicate zeolite—e.g., a hydrophilic natural or synthetic zeolite, also referred to as a molecular sieve material—or other substances with similar properties. In the depicted embodiment, the fill material 1140 comprises a multiplicity of individual solid beads or granules that absorb and release moisture while generally maintaining their individual solid shape and consistency. The fill material 1140 is surrounded and contained by the inner pouch 1136 such that the fill material is unable to escape from the inner pouch 1136. The fill material 1140 may further comprise other inert additives and physical matrices without affecting the antimicrobial and hydrous efficacies of the fill. The hydrophilic zeolite granules or beads are configured to repeatedly absorb and release moisture without substantially changing shape or form. Optionally, the fill material 1140 comprise a granular material such as activated alumina, silica gel, bentonite or hydrophilic zeolite or molecular sieve material loosely contained in the pouch or other enclosure. In alternate embodiments, the fill material comprises capsules or packets of non-granular material (e.g., gel, liquid), powder, or other materials. The fill material 1140 optionally also contains a metallic or other antimicrobial agent, such as for example silver, copper, copper oxide, gold, magnesium oxide, aluminum oxide, titanium dioxide, zinc oxide, cobalt, nickel, zirconium, molybdenum, tin, lead and/or other metals; metal oxides, metal ions, metal particles or nanoparticles; and alloys, mixtures or combinations thereof deposited therein. For example, silver or other metal loading of the fill material 1140 may be attained by the process of ion-exchange. In this process, a solution containing atomic silver, or a composition of silver, bathes or is passed through a bed of the fill granules. An ion-exchange column method may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules as known in the art may be applied to produce retention of the silver or other metals in the fill material 1140. For example, the final content by weight of an atomic silver or silver composition, or other metals or antimicrobial agents, may be as high as twenty percent of the final loaded fill granules. In example embodiments, the loaded fill granules produced by ion-exchange will exhibit high retention of the silver or other metals even under subsequent exposure to fluids and microwave irradiation. The fill granules may comprise a blend of both metal loaded and unloaded (i.e., not containing metal) zeolite or other substance(s) retaining silver or other metals. The presence of the atomic silver or other metals preferably will not interfere with the useful properties of the fill granules such as the moisture desorption, absorption, and/or adsorption properties which may be desirable in the use of the eye mask or compress system. The hydrophilic nature of example forms of zeolite fill materials provides that substantial water content is available therein and readily replenished by absorption of moisture in the form of water vapor from the atmosphere or ambient surroundings at standard room temperatures and conditions. The water so absorbed may be sufficient for moist heat delivery applications, or may be supplemented by manually added water, for providing a microwave responsive water content of the eye mask or compress system. The compositions of silver or other metals used may include but are not limited to, metal compounds, and metal salts such as silver chloride and silver nitrate.

The presence of silver or other metals within the fill granules, while optional, may provide anti-microbial properties to the therapeutic eye mask system. The ion-exchange loaded fill granules will preferably retain the silver or other metals despite microwave heating as may be required in the use of the eye mask or compress system. Further, the retention of the silver or other metals within the fill granules provides assured antimicrobial performance in a reusable and potentially washable, if so desired, moist heat therapy compress. In other embodiments, silver or other metals are incorporated into the cover material and/or other portions of the eye mask system, in addition to or instead of the fill granules. Alternatively, one or more non-metal antimicrobial materials and/or medications may optionally be incorporated into the fill material 1140, the eye coverage portions 1120, and/or other portions of the eye mask system.

The present invention also includes a method of providing moist heat therapy to a body part of a human or animal subject. In example forms, the method includes providing a therapeutic device comprising a first side, a second side, and a hydrophilic fill material contained between the first and second sides; wherein the first side at least partially comprises a moisture-transmissive material allowing passage of moisture therethrough for absorption and release into and from the fill material, and the second side at least partially comprises a moisture-impermeable material substantially preventing passage of moisture therethrough. In further example embodiments, the body part of the human or animal subject is an eye. In further example embodiments, the method also includes exposing the therapeutic device to a moisture source, such as for example, water vapor in ambient air surrounding the therapeutic device to allow absorption of moisture into the hydrophilic fill material. In further example embodiments, the method further includes exposing the therapeutic device to a heat source, such as for example, a microwave oven or other heating device to allow transfer of heat into the fill material. In further example embodiments, the method further includes directing the application of the first side of the therapeutic device into contact with the body part to provide transmission of moist heat in a first direction from the hydrophilic fill material through the moisture-transmissive material to the body part, and to substantially prevent transmission of moist heat in an opposed second direction from the hydrophilic fill material through the moisture-impermeable material away from the body part. In further example embodiments, the method further includes applying the first side of the therapeutic device into contact with the body part to provide transmission of moist heat in a first direction from the hydrophilic fill material through the moisture-transmissive material to the body part, and to substantially prevent transmission of moist heat in an opposed second direction from the hydrophilic fill material through the moisture-impermeable material away from the body part.

Figure 43:
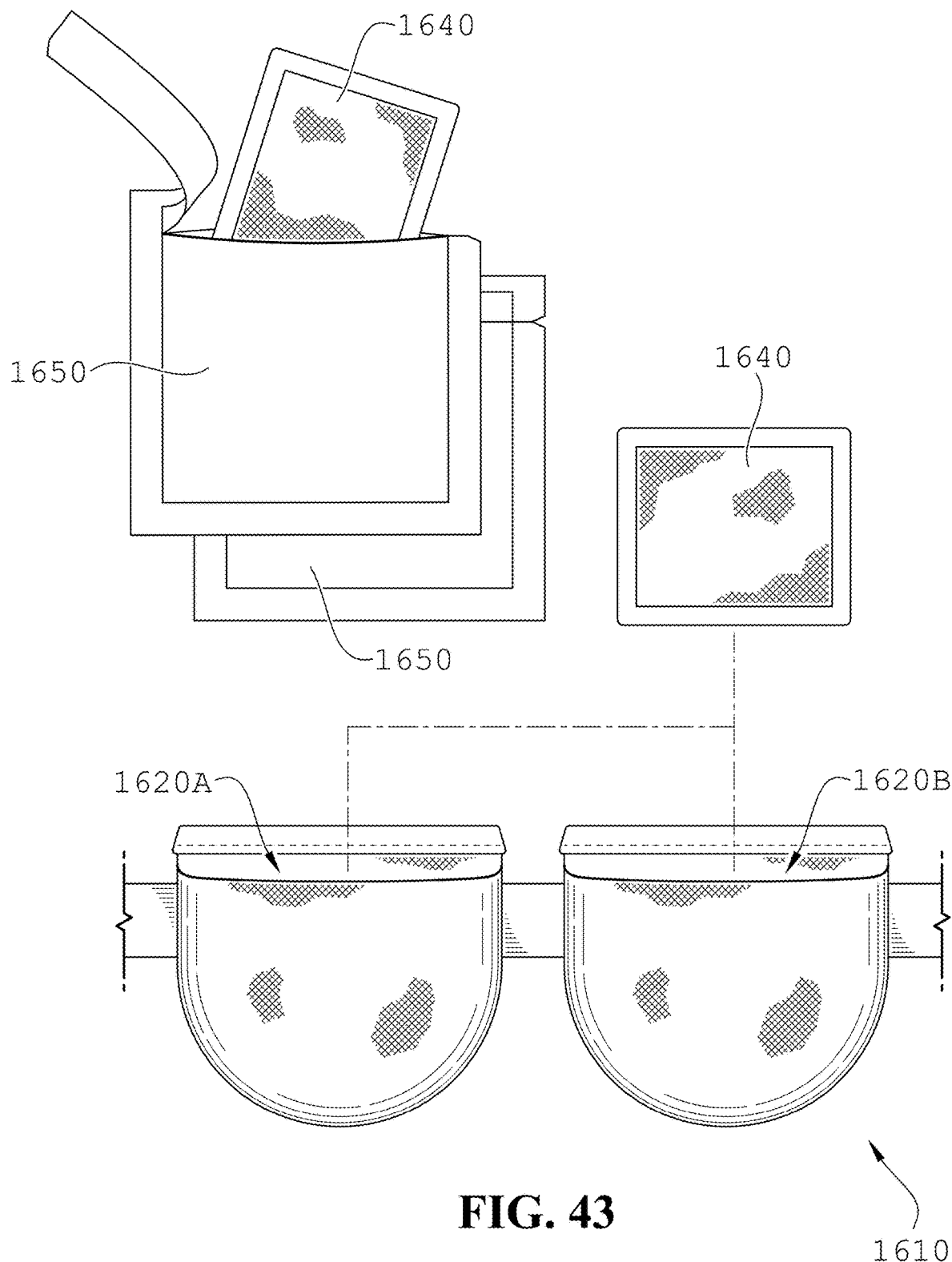
FIG. 43 shows a therapeutic eye mask or thermal compress according to another example embodiment of the invention, in combination with one or more self-heating elements.
Figure 44:
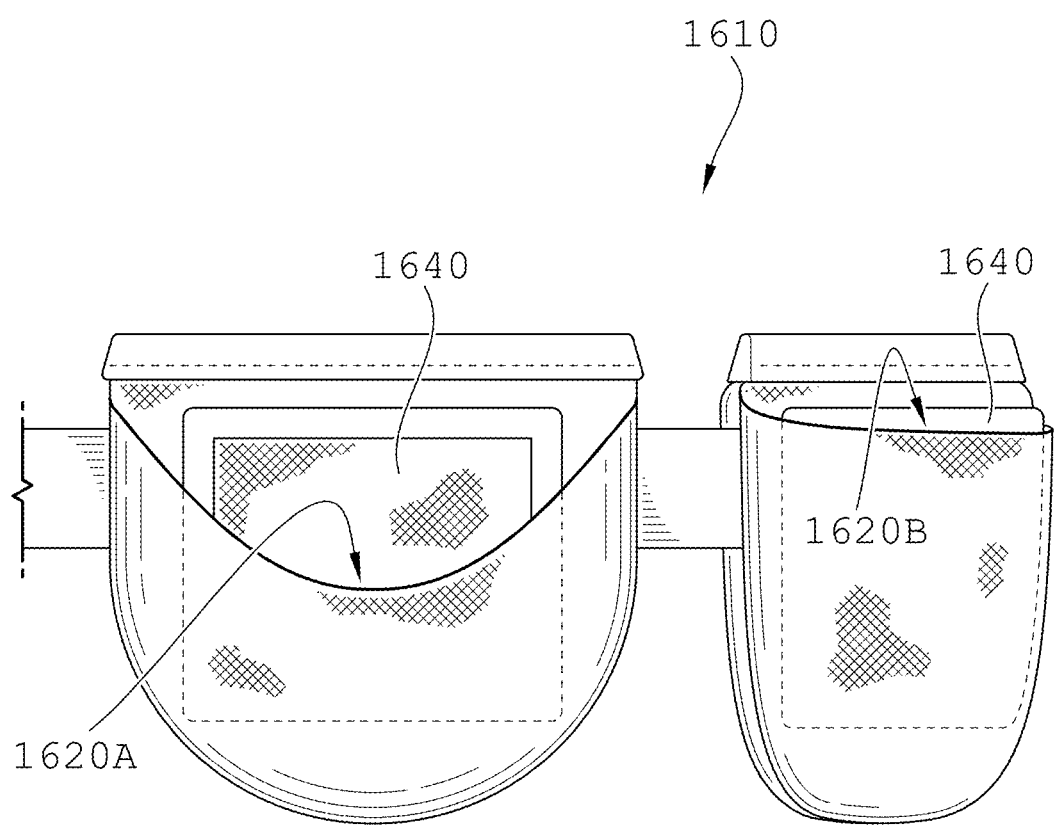
FIG. 44 shows the mask or compress of FIG. 43 with the self-heating elements installed for use.
Figure 45:
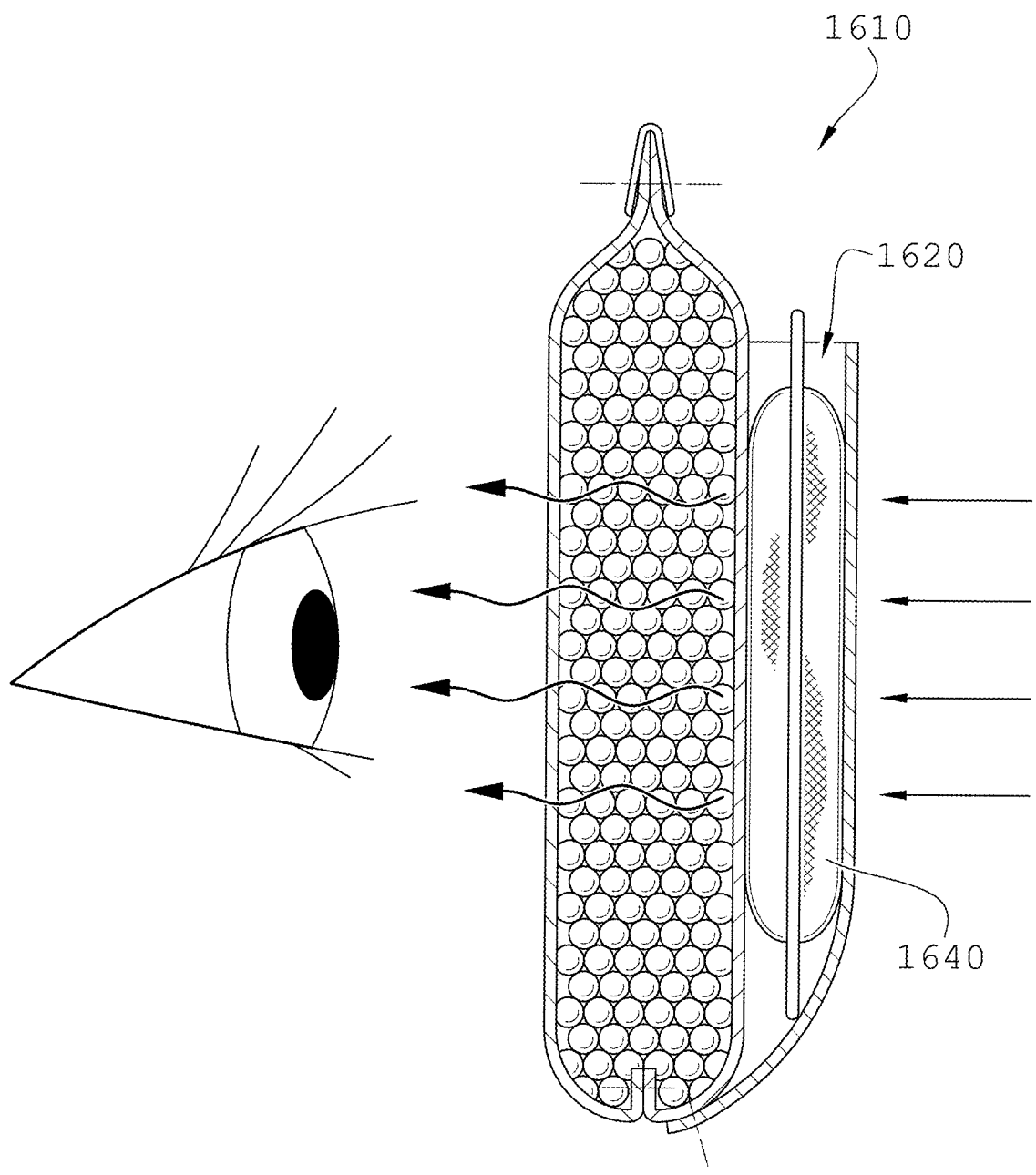
FIG. 45 schematically shows the delivery of moist heat from the mask or compress of FIG. 43 to an eye region of a user in an example mode of use.

In further example embodiments, the invention relates to a therapeutic eye mask or thermal compress system incorporating an oxygen- or otherwise-activated self-heating element for delivery of moist heat to a treated body part of a human or animal subject. With reference to FIGS. 43, 44 and 45, in example forms, the system comprises an eye mask or other therapy compress 1610, optionally including moist heat delivery capability as disclosed herein, and also including one or more receptacles or pockets 1620, for example a pair of pockets 1620A, 1620B, one arranged on each of the two eye lobes or eye-covering portions of an eye mask compress. In alternate embodiments, a single pocket may be provided on a back, neck, or otherwise configured thermal therapy compress.

The system further comprises at least one self-heating element or pod 1640, which is configured to be inserted into and removed from one of the pockets 1620 of the mask or compress 1610. For example, in an eye mask embodiment, two self-heating element or pod 1640 can be provided, one for removable insertion into each of the pair of pockets 1620A, 1620B. In example embodiments, the at least one self-heating element or pod 1640 may produce moist heat for delivery through the compress 1610 to the treated body part, and/or the self-heating element or pod may produce heat that releases moisture from other portions of the compress for delivery to the treated body part, such as for example a hydrophilic fill material such as hydrophilic zeolite particles loosely contained or packed within one or more interior compartments or enclosures of the mask or compress.

In example embodiments, the self-heating element or pod 1640 may be about 2.25"×1.75". In other embodiments one or more self-heating elements or pods of larger, smaller, or otherwise configured size and/or shape may be utilized. In example embodiments, the self-heating elements or pods 1640 comprise air- or oxygen-activated materials encapsulated in a heat-transmissive shell or envelope, for example a zinc-based oxidation type self-heating material(s) or "heat batteries," and/or other self-heating materials or processes. U.S. Pat. Nos. 9,024,360 and 9,278,796 are incorporated by reference herein by way of example. In example forms, the self-heating element or pod generates heat from an exothermic reaction that takes place when a zinc-based heating material is placed in an electrolyte solution. The zinc material uses oxygen as a cathode and zinc as the anode. Thus, when the zinc material comes into contact with oxygen from the air, zinc is converted to zinc oxide and heat is released. In other forms, the heat may be generated by exothermic reactions of calcium oxide and water, copper sulphate and zinc, powdered magnesium alloyed with iron and salt actuated with water, and/or the heat of solution of anhydrous calcium chloride.

In example embodiments, the self-heating elements or pods 1640 deliver heat at a temperature of between about 110° F.-140° F., for a duration of at least about 6-10 minutes. In alternative embodiments, the heat may be delivered at lower or higher temperatures, and/or for longer or shorter duration. The self-heating elements or pods 1640 may be disposable, recyclable, and/or reusable. In example embodiments, the system may be provided with a single mask or compress 1610 and a plurality of self-heating elements or pods 1640 for sequential use and replacement. The self-heating elements or pods 1640 may be provided in individual air or oxygen impermeable containment packages 1650, so that they may be individually activated for use by opening the package and removing the self-heating element or pod, or by removing a cover portion to allow air exposure.

For use, one or more self-heating element(s) or pod(s) 1640 is/are removed from the package 1650 or otherwise exposed to air or oxygen to activate the heating element. A self-heating element or pod 1640 is inserted into the one or more pockets 1620 of the mask or compress 1610. The mask or compress 1610 is then applied over the eyes or other body portion of a human or animal subject to be treated with thermal and/or moist heat therapy. In example embodiments, the self-heating element or pod 1640 is positioned on an external or outer side or face of the mask or compress 1610 so that heat delivered from the self-heating element or pod passes through a moisture containing fill material within the mask or compress to drive moist heat from the fill material to the eye or other treated body part, as shown in FIG. 45. In alternate embodiments, the self-heating element or pod 1640 may be installed on the internal or inner face of the mask or compress or may be inserted into an interior chamber in the mask or compress.

In still further example embodiments, the self-heating elements or pods 1640 may contain moisture or medication delivery materials, such as for example a hydrophilic zeolite material, antimicrobial silver or other metals, medication, or other materials for delivery to the treated body part upon application of heat. In further example embodiments, the self-heating element(s) or pod(s) 1640 may be integrally formed with the mask or compress 1610, optionally for disposable or one-time use. Alternatively, the self-heating element or pod(s) 1640 may be configured for removable and replaceable attachment in, on or to the mask or compress 1610. The self-heating element(s) or pod(s) 1640 may be attached in thermally conductive contact for heat transfer from the self-heating element(s) or pod(s) to the mask or compress and/or to the treated body part by means of one or more pockets or sleeves as shown, by hook-and-loop fasteners, clips, hooks, snaps, buttons, stitching, adhesive, magnets, and/or other attachment, coupling or retention means.

The features and elements of the example embodiments disclosed herein may be combined in various combinations of any two or more said features and elements, and those combinations embody additional embodiments within the scope of this disclosure.

While the invention has been described with reference to preferred and example embodiments, it will be understood by those skilled in the art that a variety of modifications, additions and deletions are within the scope of the invention, as defined by the following claims.

What is claimed is:

1. A self-heating eye mask for delivering thermal therapy to an eye region of a human subject, the eye mask comprising:
    a therapy compress comprising at least one eye-covering portion configured for application to the eye region of the human subject; and
    at least one self-heating element contained within the at least one eye-covering portion of the therapy compress, comprising at least one reactant material reactive with air to generate an exothermic reaction and release heat for delivery to the eye region of the human subject.

2. The self-heating eye mask of claim 1, wherein the at least one reactant material is selected from zinc, copper sulphate, calcium oxide, water, magnesium, iron, salt, and combinations thereof.

3. The self-heating eye mask of claim 1, further comprising a hydrophilic material, whereby heat released from the reactant material effects release of moisture from the hydrophilic material to deliver moist heat therapy to the eye region of the human subject.

4. The self-heating eye mask of claim 3, wherein the hydrophilic material comprises a hydrophilic zeolite particulate material.

5. The self-heating eye mask of claim 1, wherein the therapy compress comprises first and second eye-covering portions, each eye-covering portion containing a respective self-heating element.

6. The self-heating eye mask of claim 1, wherein the eye-covering portion comprises a pocket for receiving and containing the self-heating element.

7. The self-heating eye mask of claim 6, wherein the pocket is configured to allow removal and replacement of the self-heating element therein, whereby the eye mask is reusable.

8. The self-heating eye mask of claim 1, wherein the at least one self-heating element is integral with the eye-covering portion of the therapy compress, whereby the eye mask is disposable after one-time use.

9. The self-heating eye mask of claim 1, wherein at least a portion of the eye mask is provided in an air-impermeable containment package, and whereby opening the containment package and removal therefrom allows air exposure of the reactant material to effect the exothermic reaction and generate heat.

10. A self-heating eye mask for delivering thermal therapy to an eye region of a human subject, the eye mask comprising:
   a therapy compress comprising at least one eye-covering portion configured for application to the eye region of the human subject; and
   at least one self-heating element contained within the at least one eye-covering portion of the therapy compress, comprising at least one reactant material reactive with air to generate an exothermic reaction and release heat, and further comprising a hydrophilic material, whereby heat released from the reactant material effects release of moisture from the hydrophilic material to deliver moist heat therapy to the eye region of the human subject.

11. A self-heating eye mask for delivering thermal therapy to a human subject, the eye mask comprising:
   a therapy compress comprising first and second eye-covering portions each configured for application to a respective eye region of the human subject; and
   first and second self-heating elements, the first self-heating element contained within the first eye-covering portion of the therapy compress and the second self-heating element contained within the second eye-covering portion of the therapy compress, the first and second self-heating elements each comprising at least one reactant material reactive with air to generate an exothermic reaction and release heat for delivery to the eye region of the human subject.

12. The self-heating eye mask of claim 11, wherein the at least one reactant material is selected from zinc, copper sulphate, calcium oxide, water, magnesium, iron, salt, and combinations thereof.

13. The self-heating eye mask of claim 11, further comprising a hydrophilic material, whereby heat released from the reactant material effects release of moisture from the hydrophilic material to deliver moist heat therapy to the eye region of the human subject.

14. The self-heating eye mask of claim 13, wherein the hydrophilic material comprises a hydrophilic zeolite particulate material.

15. The self-heating eye mask of claim 11, wherein the first and second eye-covering portions each comprise a pocket for containing the respective first and second self-heating elements.

16. The self-heating eye mask of claim 15, wherein the pockets are configured to allow removal and replacement of the self-heating elements therein, whereby the eye mask is reusable.

17. The self-heating eye mask of claim 11, wherein the first and second self-heating elements are integral with the first and second eye-covering portions of the therapy compress, whereby the eye mask is disposable after one-time use.

18. The self-heating eye mask of claim 11, wherein at least a portion of the eye mask is provided in an air-impermeable containment package, and whereby opening the containment package and removal therefrom allows air exposure of the reactant material to effect the exothermic reaction and generate heat.

19. The self-heating eye mask of claim 10, wherein at least a portion of the eye mask is provided in an air-impermeable containment package, and whereby opening the containment package and removal therefrom allows air exposure of the reactant material to effect the exothermic reaction and generate heat.

20. The self-heating eye mask of claim 10, wherein the at least one reactant material is selected from zinc, copper sulphate, calcium oxide, water, magnesium, iron, salt, and combinations thereof.

21. The self-heating eye mask of claim 10, wherein the hydrophilic material comprises a hydrophilic zeolite particulate material.

22. The self-heating eye mask of claim 10, wherein the therapy compress comprises first and second eye-covering portions, each eye-covering portion containing a respective self-heating element.

23. The self-heating eye mask of claim 10, wherein the eye-covering portion comprises a pocket for receiving and containing the self-heating element.

24. The self-heating eye mask of claim 23, wherein the pocket is configured to allow removal and replacement of the self-heating element therein, whereby the eye mask is reusable.

25. The self-heating eye mask of claim 10, wherein the at least one self-heating element is integral with the eye-covering portion of the therapy compress, whereby the eye mask is disposable after one-time use.

* * * * *